United States Patent
Sobhany

(10) Patent No.: US 11,186,241 B2
(45) Date of Patent: Nov. 30, 2021

(54) AUTOMATED EMOTION DETECTION AND ENVIRONMENTAL RESPONSE

(71) Applicant: Cobalt Industries Inc., San Francisco, CA (US)

(72) Inventor: Rana June Sobhany, Lakewood Ranch, FL (US)

(73) Assignee: COBALT INDUSTRIES INC., San Francisco, CA (US)

( * ) Notice: Subject to any disclaimer, the term of this patent is extended or adjusted under 35 U.S.C. 154(b) by 0 days.

(21) Appl. No.: 16/777,830

(22) Filed: Jan. 30, 2020

(65) Prior Publication Data
US 2020/0239002 A1    Jul. 30, 2020

Related U.S. Application Data

(60) Provisional application No. 62/957,727, filed on Jan. 6, 2020, provisional application No. 62/948,745, filed (Continued)

(51) Int. Cl.
*B60W 40/08*    (2012.01)
*G05D 1/00*    (2006.01)
(Continued)

(52) U.S. Cl.
CPC .............. *B60R 16/037* (2013.01); *A61B 5/18* (2013.01); *B60H 1/00878* (2013.01); (Continued)

(58) Field of Classification Search
CPC ......... B60W 40/08; B60W 2040/0872; B60W 2040/089; B60W 50/085; B60W 50/08; (Continued)

(56) References Cited

U.S. PATENT DOCUMENTS 7,924,146 B2    4/2011    Seder et al.
8,072,686 B2    12/2011    Cui et al.
(Continued)

FOREIGN PATENT DOCUMENTS

DE    102018217634 A1    11/2019
WO    2018211301 A1    11/2018

OTHER PUBLICATIONS

Nitze-Nelson, Dre , "Riding with Empathy. Let's talk about In-Vehicle Sensing", Retrieved from: https://www.linkedin.com/pulse/riding-empathy-lets-talk-in-vehicle-sensing-dr%C3%A9-nitze-nelson, Jan. 2020.

*Primary Examiner* — B M M Hannan
(74) *Attorney, Agent, or Firm* — Perkins Coie LLP

(57) ABSTRACT

A processor associated with a vehicle receives sensor data from a plurality of sensors associated with a vehicle, where each sensor generates data corresponding to a different parameter of a passenger in the vehicle. Based on the sensor data, one or more primitive emotional indications are generated. The processor applies a model to the one or more primitive emotional indications that when applied outputs a contextualized emotional indication associated with the passenger that includes an assessment of an emotional state of the passenger and a reason for the emotional state. A contextual response is selected based on the contextualized emotional indication, and the processor causes an output by the vehicle to enact the contextual response.

22 Claims, 18 Drawing Sheets

Related U.S. Application Data on Dec. 16, 2019, provisional application No. 62/937,414, filed on Nov. 19, 2019, provisional application No. 62/798,721, filed on Jan. 30, 2019.

(51) Int. Cl.

| | | |
|---|---|---|
| *B60R 16/037* | (2006.01) | |
| *G06F 16/2457* | (2019.01) | |
| *G06F 16/23* | (2019.01) | |
| *B60W 30/02* | (2012.01) | |
| *B60H 1/00* | (2006.01) | |
| *B60H 3/00* | (2006.01) | |
| *B60N 2/90* | (2018.01) | |
| *G06N 20/00* | (2019.01) | |
| *G06K 9/62* | (2006.01) | |
| *H04L 12/40* | (2006.01) | |
| *B60W 50/08* | (2020.01) | |
| *G05B 13/02* | (2006.01) | |
| *G06N 5/04* | (2006.01) | |
| *A61B 5/18* | (2006.01) | |
| *B60K 35/00* | (2006.01) | |
| *G06F 3/01* | (2006.01) | |
| *G06K 9/00* | (2006.01) | |
| *G10L 25/63* | (2013.01) | |
| *H04L 29/08* | (2006.01) | |
| *B60W 50/00* | (2006.01) | |

(52) U.S. Cl.
CPC ........... *B60H 3/0007* (2013.01); *B60K 35/00* (2013.01); *B60N 2/976* (2018.02); *B60W 30/025* (2013.01); *B60W 40/08* (2013.01); *B60W 50/08* (2013.01); *B60W 50/085* (2013.01); *G05B 13/028* (2013.01); *G05D 1/0088* (2013.01); *G06F 3/011* (2013.01); *G06F 3/017* (2013.01); *G06F 16/2379* (2019.01); *G06F 16/24575* (2019.01); *G06K 9/00315* (2013.01); *G06K 9/00892* (2013.01); *G06K 9/6267* (2013.01); *G06K 9/6292* (2013.01); *G06N 5/04* (2013.01); *G06N 20/00* (2019.01); *G10L 25/63* (2013.01); *H04L 12/40* (2013.01); *H04L 67/306* (2013.01); *B60W 2040/089* (2013.01); *B60W 2040/0872* (2013.01); *B60W 2050/0028* (2013.01); *B60W 2050/0088* (2013.01); *B60W 2540/22* (2013.01); *B60W 2540/221* (2020.02); *B60W 2710/30* (2013.01); *B60W 2754/20* (2020.02); *H04L 2012/40215* (2013.01)

(58) Field of Classification Search
CPC ....... B60W 30/025; B60W 2050/0088; B60W 2050/0028; B60W 2754/20; B60W 2710/30; B60W 2540/22; B60W 2540/221; G10L 25/63; B60K 35/00; B60K 2370/143; B60K 2370/149; B60K 37/06; G06K 9/00315; G06K 9/00892; G06K 9/6267; G06K 9/6292; A61B 5/18; A61B 5/165; A61B 5/163; A61B 2562/0219; A61B 2562/0252; A61B 5/7267; A61B 5/7246; A61B 2560/0242; A61B 2560/0475; A61B 5/7275; A61B 2562/0271; G06F 3/017; G06F 3/011; G06F 16/24575; G06F 16/2379; G06F 2203/011; B60R 16/037; H04L 67/306; H04L 12/40; H04L 2012/40215; H04L 12/4641; G05B 13/028; G05B 2219/2642; G05B 15/02; G06N 5/04; G06N 20/00; G05D 1/0088; B60H 1/00878; B60H 3/0007; B60N 2/976

USPC ........................................................... 701/1
See application file for complete search history.

(56) References Cited

U.S. PATENT DOCUMENTS

| | | |
|---|---|---|
| 8,269,652 B2 | 9/2012 | Seder et al. |
| 8,317,329 B2 | 11/2012 | Seder et al. |
| 8,330,673 B2 | 12/2012 | Cui et al. |
| 8,344,894 B2 | 1/2013 | Szczerba et al. |
| 8,350,724 B2 | 1/2013 | Szczerba et al. |
| 8,358,224 B2 | 1/2013 | Seder et al. |
| 8,384,531 B2 | 2/2013 | Szczerba et al. |
| 8,384,532 B2 | 2/2013 | Szczerba et al. |
| 8,395,529 B2 | 3/2013 | Seder et al. |
| 8,427,395 B2 | 4/2013 | Seder et al. |
| 8,482,486 B2 | 7/2013 | Seder et al. |
| 8,547,298 B2 | 10/2013 | Szczerba et al. |
| 8,564,502 B2 | 10/2013 | Cui et al. |
| 8,629,784 B2 | 1/2014 | Szczerba et al. |
| 8,629,903 B2 | 1/2014 | Seder et al. |
| 8,704,653 B2 | 4/2014 | Seder et al. |
| 8,775,063 B2 | 7/2014 | Zeng |
| 8,817,090 B2 | 8/2014 | Szczerba et al. |
| 8,830,141 B2 | 9/2014 | Seder et al. |
| 8,912,978 B2 | 12/2014 | Szczerba et al. |
| 9,162,622 B2 | 10/2015 | Szczerba et al. |
| 9,988,055 B1 | 6/2018 | O'Flaherty et al. |
| 10,393,530 B2* | 8/2019 | Cremer ................. H04W 4/021 |
| 10,525,850 B1 | 1/2020 | Tang et al. |
| 10,599,144 B2 | 3/2020 | Zheng et al. |
| 2005/0125117 A1 | 6/2005 | Breed |
| 2006/0149428 A1* | 7/2006 | Kim ....................... B60W 40/09 701/1 |
| 2007/0124027 A1* | 5/2007 | Betzitza ................ B60W 40/02 701/1 |
| 2008/0119994 A1* | 5/2008 | Kameyama ........... B60W 40/08 701/48 |
| 2010/0134302 A1 | 6/2010 | Ahn et al. |
| 2010/0253542 A1 | 10/2010 | Seder et al. |
| 2011/0224875 A1* | 9/2011 | Cuddihy ............... B60W 10/18 701/42 |
| 2014/0188920 A1 | 7/2014 | Sharma et al. |
| 2014/0309893 A1* | 10/2014 | Ricci ..................... B60W 50/14 701/49 |
| 2015/0091740 A1* | 4/2015 | Bai ......................... B60Q 9/008 340/901 |
| 2015/0243172 A1 | 8/2015 | Eskilson |
| 2015/0360608 A1* | 12/2015 | Tzirkel-Hancock ..... B60Q 9/00 297/217.1 |
| 2015/0363986 A1 | 12/2015 | Hoyos et al. |
| 2016/0001781 A1 | 1/2016 | Fung et al. |
| 2017/0021282 A1* | 1/2017 | Comploi ............... B60W 50/10 |
| 2017/0139411 A1 | 5/2017 | Hartung et al. |
| 2017/0200449 A1 | 7/2017 | Penilla et al. |
| 2017/0247000 A1 | 8/2017 | Ricci |
| 2017/0318044 A1 | 11/2017 | Dagmi et al. |
| 2017/0370732 A1* | 12/2017 | Bender ............. G01C 21/3492 |
| 2018/0034656 A1 | 2/2018 | Balasubramanian et al. |
| 2018/0050696 A1 | 2/2018 | Misu et al. |
| 2018/0118218 A1* | 5/2018 | Miloser ................ B60W 10/30 |
| 2018/0174457 A1 | 6/2018 | Taylor |
| 2018/0178808 A1 | 6/2018 | Zhao et al. |
| 2018/0182185 A1 | 6/2018 | Tong et al. |
| 2018/0241852 A1 | 8/2018 | Maluf et al. |
| 2018/0248766 A1 | 8/2018 | Ezra et al. |
| 2018/0268567 A1 | 9/2018 | Hart et al. |
| 2018/0364966 A1 | 12/2018 | Valeri et al. |
| 2019/0028766 A1 | 1/2019 | Wold et al. |
| 2019/0049957 A1 | 2/2019 | Healey et al. |
| 2019/0073547 A1 | 3/2019 | El Kaliouby et al. |
| 2019/0171409 A1* | 6/2019 | Boulanger ........... G06F 16/638 |
| 2019/0213429 A1 | 7/2019 | Sicconi et al. |
| 2019/0219413 A1 | 7/2019 | Prakah-asante |
| 2019/0232974 A1 | 8/2019 | Reiley et al. |
| 2019/0265712 A1 | 8/2019 | Satzoda et al. |
| 2020/0036592 A1 | 1/2020 | Kholaif |

(56) References Cited

U.S. PATENT DOCUMENTS

| | | |
|---|---|---|
| 2020/0039520 A1 | 2/2020 | Misu et al. |
| 2020/0039521 A1 | 2/2020 | Misu et al. |
| 2020/0073478 A1* | 3/2020 | An .................. G06F 3/011 |
| 2020/0079385 A1 | 3/2020 | Beaurepaire et al. |
| 2020/0110461 A1* | 4/2020 | Trim ............... H04N 21/25891 |

\* cited by examiner

800

| ACQUIRE USER CHARACTERISTIC INFORMATION 802 | GENERATE A USER PROFILE 804 | IDENTIFY USER(S) IN THE VEHICLE 806 | DETECT AN EMOTIONAL STATE OF THE USER 808 | GENERATE USER-SPECIFIC OUTPUT ACTIONS 810 |

AUTOMATED EMOTION DETECTION AND ENVIRONMENTAL RESPONSE

CROSS-REFERENCE TO RELATED APPLICATIONS

This application claims the benefit of U.S. Provisional Patent No. 62/798,721, filed Jan. 30, 2019; U.S. Provisional Patent No. 62/937,414, filed Nov. 19, 2019; U.S. Provisional Patent No. 62/948,745, filed Dec. 16, 2019; and U.S. Provisional Patent No. 62/957,727, filed Jan. 6, 2020, each of which is incorporated herein by reference in its entirety.

This application is related to U.S. patent application Ser. No. 16/777,828, filed Jan. 30, 2020, U.S. patent application Ser. No. 16/777,843, filed Jan. 30, 2020, U.S. patent application Ser. No. 16/777,844, filed Jan. 30, 2020, and U.S. patent application Ser. No. 16/777,850, filed Jan. 30, 2020, each of which is incorporated herein by reference in its entirety.

TECHNICAL FIELD

This disclosure relates to modifying features of a vehicle based on detected characteristics of the environment surrounding the vehicle.

BACKGROUND

Vehicles are generally utilized by individuals for transportation to various destinations. For example, a vehicle can include a car, truck, train, airplane, etc. While vehicles are generally utilized for transportation, vehicles include components configured to perform various functionalities.

For example, a vehicle can include components configured to modify the playback of entertainment content (e.g., audio, video, gaming content). As another example, the vehicle includes components configured to control an internal environment of the vehicle. These components are generally included in a vehicle to increase a user experience while in the vehicle.

In many cases, a user may modify various components of the vehicle using various interfaces (an interactive display, a set of dials, buttons, etc.), where modification of these components are generally performed responsive to detecting a modification to an interface performed by the user.

Further, each user in a vehicle generally has a set of unique desired settings of components in the vehicle. For instance, a first user may want audio playing from speakers in the vehicle at a first volume, while a second user may want no audio playing and a set of fans in the vehicle operating at a high speed.

Moreover, the set of unique desired settings for a user may differ based on other aspects. For example, such aspects that can differ the set of unique desired settings for the user can include an emotional state of the user, the time of day, external weather conditions, etc.

DETAILED DESCRIPTION

Overview

Automotive vehicles have a wide variety of sensor hardware available and are continuously adding new capabilities as technology improves and costs reduce. However, the data produced by the sensors is typically trapped in silos for single-use purpose, resulting an enormous universe of untapped data available in automotive vehicles. A vehicle experience system uses these sensor inputs to create a personalized, contextually-aware and real-time adaptive experience for drivers and/or passengers of vehicles. Various embodiments of the vehicle experience system described herein can measure an emotional state of a driver or passenger in a vehicle, as well as context of the vehicle or its environment, and control entertainment, safety, or comfort systems of the vehicle in manner that is dynamically responsive to the person's emotional state, the context of the vehicle or environment, or a combination thereof. To control the systems of the vehicle, various embodiments of the vehicle experience system create, train, and utilize personalized models that learn a person's emotional states, habits, and reactions over time to improve the ability of the vehicle to respond to or anticipate a person's needs.

Some embodiments of the vehicle experience system are described herein with respect to vehicles, including measuring parameters in vehicles and controlling outputs associated with the vehicles to create dynamic, personalized vehicle experiences. However, the experience system described herein is not limited to vehicles. Similar methodologies and systems can be implemented in other environments in which people spend time or pass through, including homes, office buildings, hotels, restaurants, transit stations, or schools.

System Overview

The present embodiments relate to vehicle passenger experience and personalization. Embodiments of systems and processes described herein create a personalized, adaptable experience in a vehicle that can be based on data fused from multiple sensors in a vehicle.

Environment Overview

Figure 1:
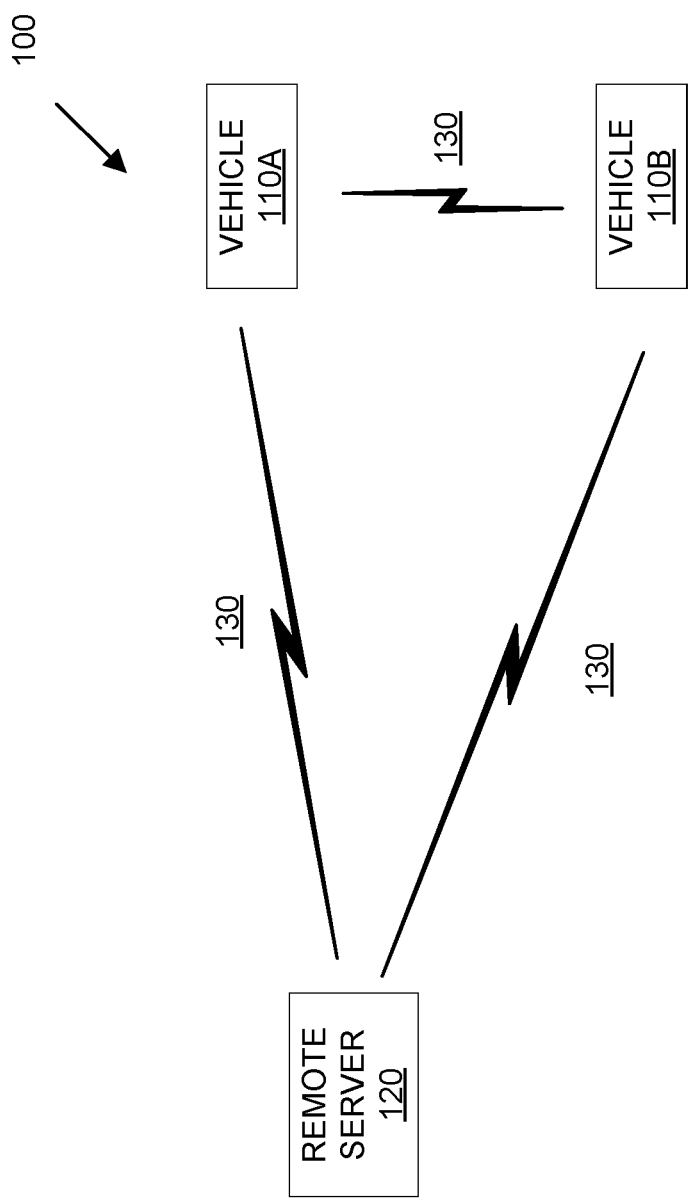
FIG. 1 is an example environment that includes one or more vehicles and one or more remote servers.

FIG. 1 is an example environment 100 that includes one or more vehicles 110 and one or more remote servers 120.

The vehicle 110 can include any vehicle capable of carrying one or more passengers, including any type of land-based automotive vehicle (such as cars, trucks, or buses), train, flying vehicle (such as airplanes, helicopters, or space shuttles), or aquatic vehicle (such as cruise ships). The vehicle 110 can be a vehicle operated by any driving mode, including fully manual (human-operated) vehicles, self-driving vehicles, or hybrid-mode vehicles that can switch between manual and self-driving modes. As used herein, a "self-driving" mode is a mode in which the vehicle 110 operates at least one driving function in response to real-time feedback of conditions external to the vehicle 110 and measured automatically by the vehicle 110. The driving functions can include any aspects related to control and operation of the vehicle, such as speed control, direction control, or lane positioning of the vehicle 110. To control the driving functions, the vehicle 110 can receive real-time feedback from external sensors associated with the vehicle 110, such as sensors capturing image data of an environment around the vehicle 110, or sources outside the vehicle 110, such as another vehicle or the remote server 120. The vehicle 110 can process the sensor data to, for example, identify positions and/or speeds of other vehicles proximate to the vehicle 110, track lane markers, identify non-vehicular entities on the road such as pedestrians or road obstructions, or interpret street signs or lights. In some cases, the vehicle 110 operates in an autonomous mode under some driving circumstances, such that the driver does not need to control any driving functions during the autonomous operation. In other cases, the vehicle 110 controls one or more driving functions while the driver concurrently controls one or more other driving functions.

The vehicle 110 can have a regular driver, or a person who is usually driving the vehicle when the vehicle is operated. This person may, for example, be an owner of the vehicle 110. In other cases, the vehicle 110 can be a shared vehicle that does not have a regular driver, such as a rental vehicle or ride-share vehicle.

In some embodiments, a vehicle 110 can retrieve a user profile that is associated with a user that primarily operates the vehicle. In other embodiments, upon detecting a user in the vehicle (e.g., by an indication from a mobile device, facial recognition), a unique user profile associated with the user can be retrieved. Based on the user profile, user-specific output actions can be performed that modify various settings in the vehicle.

The remote server 120 can process or store data received from the vehicle 110, or can send data to the vehicle 110. In various embodiments, the remote server 120 can include data processing and analysis functionality to, for example, determine a context of an interior or exterior of the vehicle 110. Other embodiments of the remote server 120 can communicate content to the vehicle 110, including media content or remote updates to software or configuration settings of the vehicle 110. The remote server 120 can be configured as a physical server, a cloud computing platform, or any other suitable configuration.

The remote server 120 and vehicle 110 can communicate over one or more network channels 130, which can include any of a variety of individual connections via the internet such as cellular or other wireless networks, such as 4G networks, 5G networks, or WiFi. In some embodiments, the network may connect terminals, services, and mobile devices using direct connections such as radio-frequency identification (RFID), near-field communication (NFC), Bluetooth™, low-energy Bluetooth™ (BLE), WiFi™, ZigBee™, ambient backscatter communications (ABC) protocols, USB, or LAN. Because the information transmitted may be personal or confidential, security concerns may dictate one or more of these types of connections be encrypted or otherwise secured. In some embodiments, however, the information being transmitted may be less personal, and therefore the network connections may be selected for convenience over security. The network may comprise any type of computer networking arrangement used to exchange data. For example, the network may be the Internet, a private data network, virtual private network using a public network, and/or other suitable connection(s) that enables components in system environment 100 to send and receive information between the components of system environment 100. The network may also include a public switched telephone network ("PSTN") and/or a wireless network.

The vehicles 110A, 110B can also communicate with each other by communicating either indirectly through the remote server 120 or directly over a vehicle-to-vehicle communications channel 130.

Vehicle Environment Overview

Figure 2:
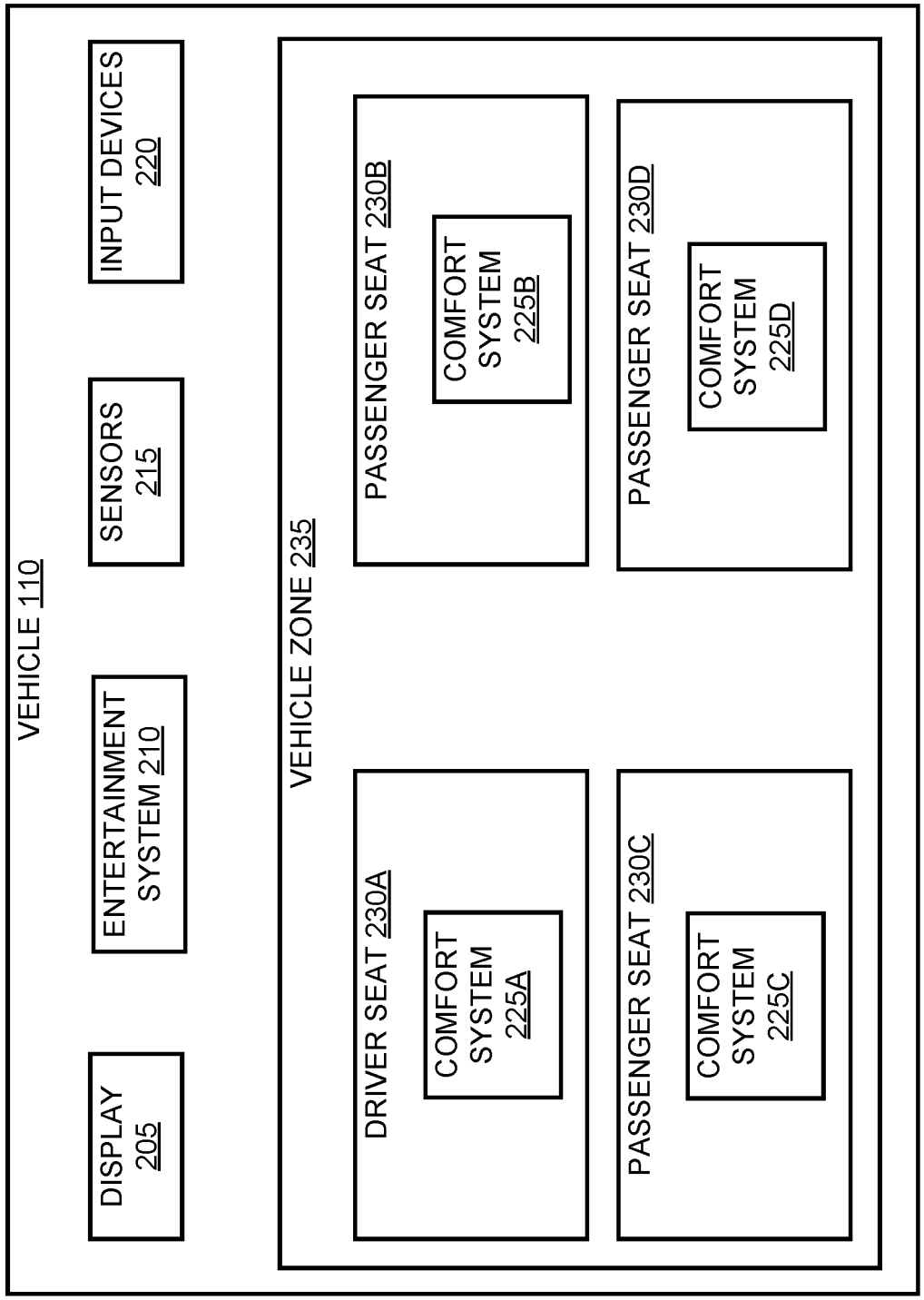
FIG. 2 is a schematic diagram illustrating an example vehicle.

FIG. 2 is a schematic diagram illustrating an example vehicle 110. The vehicle 110 can include one or more seats 230 in which passengers can be seated while they ride in the vehicle. By way of example, FIG. 2 illustrates a driver seat 230A and three passenger seats 230B, 230C, and 230D, but the vehicle 110 can have any number of seats and can configure the seats differently. Further, in FIG. 2, the vehicle 110 can include a vehicle zone 235 that includes a region that includes the interior of the vehicle.

As shown in FIG. 2, the vehicle 110 can have one or more displays 205. The one or more displays 205 can include a dedicated, persistent display, such as a display associated with an infotainment system of the vehicle 110 or a head-up display positioned within a field of vision of a driver while the driver is driving the vehicle 110. Additionally or alternatively, the one or more displays 205 can include devices that are used to display content only under some circumstances. For example, any glass in the vehicle—such as a windshield, one or more side windows, or a rearview or side mirror—can be activated to be used as a display device 205. When the display features of the glass are not activated, the glass can be, for example, transparent, to allow passengers to see through the glass to an exterior of the vehicle, or reflective, to enable passengers to view behind or to the side of the vehicle.

In some embodiments, the display 205 is a head-up display positioned in or near the driver's field of view to display content in a manner that is visible but does not obstruct the driver's view of the road while driving. For example, the head-up display may be positioned near a bottom of a windshield. Alternatively, the head-up display may be positioned near a top of the windshield or on a side of the windshield away from a central field of view while the driver is looking forward. Furthermore, the head-up display may be integrated into the windshield or a display device separate from the windshield. The head-up display may be translucent or transparent to reduce obstruction. In some embodiments, the head-up display displays content related to driving of the vehicle 110 while the vehicle is being driven. For example, the head-up display can display speed, navigation instructions, a measurement of a distance to the next car, or fuel level or battery charge status.

In some embodiments, the head-up display has a first size while the vehicle 110 is being driven, and a second size when the vehicle 110 is not being driven. Alternatively, content can be displayed within an area of the head-up display that has a first size while the vehicle 110 is being driven, while the content can be displayed in an area that has a second size when the vehicle is not being driven. For example, if a driver is consuming media content while recharging a battery of the vehicle 110, the head-up display can be changed to a stationary mode in which a larger portion of the windshield is used to the display the media content. The larger portion of the windshield can include an entirety of the windshield, or a portion of the windshield that is larger than the portion used by the head-up display while the vehicle is driven. In some embodiments, a size of a display can change based on an operation state of the vehicle. For example, when the vehicle transitions from an operating state to an idle state, the size of the display can be increased.

The vehicle 110 can have an entertainment system 210. The entertainment system 210 can provide entertainment content to passengers in the vehicle 110, and can include one or more output devices in the vehicle that are configured to output the entertainment content to the passengers. The output devices can include the displays 205 to display video, image, or textual content and a sound system including one or more speakers to play audio content. In some cases, the output devices associated with the entertainment system 210 can further include lighting systems in the interior of the vehicle or tactile output devices such as a vibrating device in the seats 230. The entertainment system 210 can output entertainment content for an entire interior of the vehicle 110 at the same time, or can provide different content for different zones in the vehicle 110. For example, referring to FIG. 2, the entertainment system 210 can output entertainment content for the vehicle zone 235, or can output first entertainment content for a person in the driver seat 230A and second entertainment content for a person in the passenger seat 230B. Some embodiments of the entertainment system 210 automatically recommend and/or select entertainment content for output to a user.

The vehicle 110 can include a plurality of sensors 215 configured to generate data related to parameters inside the vehicle 110 and outside the vehicle 110, including parameters related to one or more passengers inside the vehicle. Example parameters that can be measured by the sensors 215 include vehicle speed, acceleration, lane position, steering angle, in-cabin decibel level, audio volume level, current information displayed by a multimedia interface in the vehicle, force applied by the user to the multimedia interface, ambient light, humidity level, raw video feed (whether from sources internal or external to the vehicle), audio input, user metadata, user state, calendar data, user observational data, contextual external data, traffic conditions, weather conditions, in-cabin occupancy information, road conditions, user drive style, or non-contact biofeedback. Thus, example sensors 215 include internal or external cameras, eye tracking sensors, temperature sensors, audio sensors, weight sensors in a seat 230, force sensors measuring force applied to devices such as a steering wheel or display 205, accelerometers, gyroscopes, light detecting and ranging (LIDAR) sensors, or infrared sensors. Some of the sensors 215 can, at least in part, be used for biosensing, such as identifying that one or more people or animals are in a vehicle, determining where the people, objects, or animals are located in the vehicle, or identifying emotional states of a person in a vehicle.

The vehicle 110 can include one or more input devices 220. At least one of the input devices 220 can be a device configured to receive a tactile input from a passenger. For example, the vehicle 110 may include an infotainment system with soft or hard buttons the user can touch to provide an input into the vehicle. One or more of the sensors 215 can additionally or alternatively be used as an input device 220. For example, one of the sensors 215 can be a camera configured to capture image data of a passenger that can be input to a gaze tracking tool. The passenger's gaze, as tracked by the gaze tracking tool, can be used as an input signal to control aspects of the vehicle 110. For example, the vehicle 110 can determine that a passenger has selected an item displayed on the display 205 by determining that the passenger is looking at the displayed item. Similarly, gesture tracking, voice recognition, or biometric systems can be used as input devices 220 that enable a passenger to provide explicit inputs to the vehicle 110 to make selections or adjust parameters of the vehicle 110. The vehicle 110 can have one or more input devices 220 associated with a passenger.

Some of the input devices 220 can include portions of the vehicle 110 that can be used in a first state to control an aspect of the vehicle related to driving the vehicle, while also being usable in a second state to provide input to the media system. For example, the vehicle 110 can include a steering wheel that is used in a first state to steer the vehicle and used in a second state as a controller for video game content provided by the media system. Other example uses of the steering wheel in the second state include navigating a menu (e.g., turn the steering wheel to the right to scroll forward in the menu and turn the steering wheel to the left to select an item in the menu), skipping forward or backward in a video or audio track (e.g., turn the steering wheel to the right to skip forward and to the left to skip backward), or increasing or decreasing the size of text or images displayed on the display 205 (e.g., turn the steering wheel to the right to increase text font size and to the left to decrease the font size). Other devices in the vehicle 110 may likewise have different functions in different states, such as a gear shift, a brake pedal, or a turn signal lever.

In still other cases, the input devices 220 include one or more interfaces that receive a signal from a device that is not integrated into the vehicle 110. For example, the input devices 220 can include an interface configured to receive a signal from a mobile device or wearable device (such as a smart phone, smart watch, smart glasses, or tablet), such that the driver can provide inputs to the vehicle 110 via the mobile or wearable device.

The vehicle 110 can have a comfort system 225. The comfort system 225 can include one or more components with adjustable parameters that facilitate comfort of passengers in the vehicle 110. Example components of the comfort system include air temperature control components (such as an air conditioning or heating system), air quality control components (such as a humidity or air purification system), seat warmers, seat position controls, or chair massagers. In some embodiments, as shown in FIG. 2, the comfort system 225 can include one or more subsystems to regulate comfort parameters for each seat 230 in the vehicle. Thus, for example, the comfort system 225 can include a first comfort system 225A corresponding to the driver seat 230A, a second comfort system 225B corresponding to the passenger seat 230B, and so forth. In other embodiments, the comfort system is a centralized control system that defines parameters for comfort components throughout the vehicle, which may or may not be individualized to each seat 230.

Figure 3:
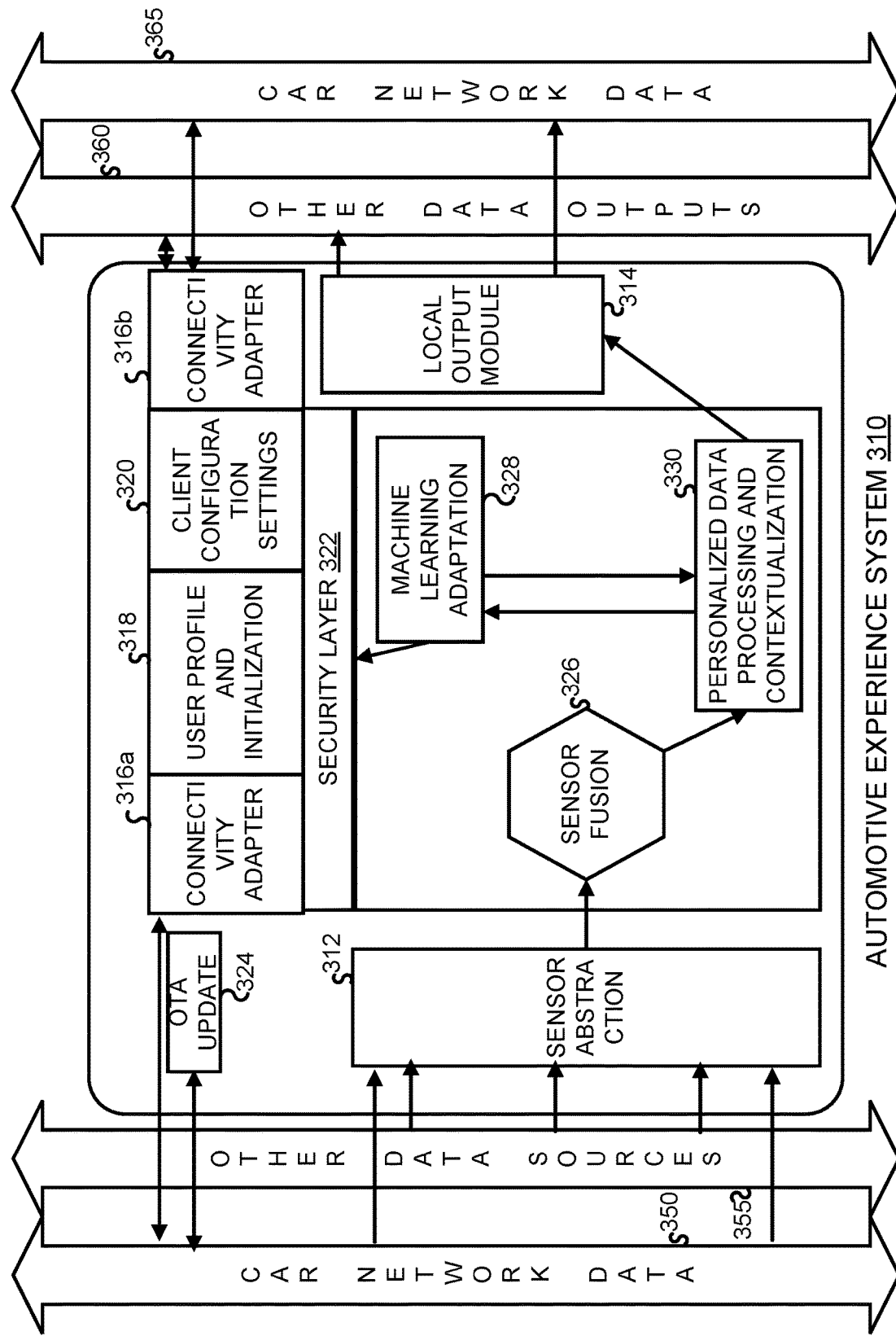
FIG. 3 is a block diagram illustrating components of a vehicle, according to some embodiments.

FIG. 3 is a block diagram illustrating components of a vehicle 110, according to some embodiments.

As shown in FIG. 3, the vehicle 110 can include a vehicle experience system 310. The vehicle experience system 310 controls an experience for passengers in the vehicle 110. The vehicle experience system 310 can include computer software and hardware to execute the software, special-purpose hardware, or other components to implement the functionality of the media system 120 described herein. For example, the vehicle experience system 310 can include programmable circuitry (e.g., one or more microprocessors), programmed with software and/or firmware, entirely in special-purpose hardwired (i.e., non-programmable) circuitry, or in a combination or such forms. Special-purpose circuitry can be in the form of, for example, one or more application-specific integrated circuits (ASICs), programmable logic devices (PLDs), field-programmable gate arrays (FPGAs), etc. In some embodiments, the vehicle experience system is implemented using hardware in the vehicle 110 that also performs other functions of the vehicle. For example, the vehicle experience system can be implemented within an infotainment system in the vehicle 110. In other embodiments, components such as one or more processors or storage devices can be added to the vehicle 110, where some or all functionality of the vehicle experience system is implemented on the added hardware.

The vehicle experience system 310 can read and write to a car network 350. The car network 350, implemented for example as a controller area network (CAN) bus inside the vehicle 110, enables communication between components of the vehicle, including electrical systems associated with driving the vehicle (such as engine control, anti-lock brake systems, parking assist systems, and cruise control) as well as electrical system associated with comfort or experience in the interior of the vehicle (such as temperature regulation, audio systems, chair position control, or window control). The vehicle experience system 310 can also read data from or write data to other data sources 355 or other data outputs 360, including one or more other on-board buses (such as a local interconnect network (LIN) bus or comfort-CAN bus), a removable or fixed storage device (such as a USB memory stick), or a remote storage device that communicates with the vehicle experience system over a wired or wireless network.

The CAN bus 350 or other data sources 355 provide raw data from sensors inside or outside the vehicle, such as the sensors 215. Example types of data that can be made available to the vehicle experience system 310 over the CAN bus 350 include vehicle speed, acceleration, lane position, steering angle, in-cabin decibel level, audio volume level, current information displayed by a multimedia interface in the vehicle, force applied by the user to the multimedia interface, ambient light, or humidity level. Data types that may be available from other data sources 355 include raw video feed (whether from sources internal or external to the vehicle), audio input, user metadata, user state, calendar data, user observational data, contextual external data, traffic conditions, weather conditions, in-cabin occupancy information, road conditions, user drive style, or non-contact biofeedback. Any of a variety of other types of data may be available to the vehicle experience system 310.

Some embodiments of the vehicle experience system 310 process and generate all data for controlling systems and parameters of the vehicle 110, such that no processing is done remotely (e.g., by the remote server 120). Other embodiments of the vehicle experience system 310 are configured as a layer interfacing between hardware components of the vehicle 110 and the remote server 120, transmitting raw data from the car network 350 to the remote server 120 for processing and controlling systems of the vehicle 110 based on the processing by the remote server 120. Still other embodiments of the vehicle experience system 310 can perform some processing and analysis of data while sending other data to the remote server 120 for processing. For example, the vehicle experience system 310 can process raw data received over the CAN bus 350 to generate intermediate data, which may be anonymized to protect privacy of the vehicle's passengers. The intermediate data can be transmitted to and processed by the remote server 120 to generate a parameter for controlling the vehicle 110. The vehicle experience system 310 can in turn control the vehicle based on the parameter generated by the remote server 120. As another example, the vehicle experience system 310 can process some types of raw or intermediate data, while sending other types of raw or intermediate data to the server 120 for analysis.

Some embodiments of the vehicle experience system 310 can include an application programing interface (API) enabling remote computing devices, such as the remote server 120, to send data to or receive data from the vehicle 110. The API can include software configured to interface between a remote computing device and various components of the vehicle 110. For example, the API of the vehicle experience system 310 can receive an instruction to apply a parameter to the vehicle from a remote device, such as a parameter associated with entertainment content, and apply the parameter to the vehicle.

As shown in FIG. 3, some embodiments of the vehicle experience system 310 can include a sensor abstraction component 312, an output module 314, a connectivity adapter 316a-b, a user profile module 318, a settings module 320, a security layer 322, an over the air (OTA) update module 324, a processing engine 330, a sensor fusion module 326, and a machine learning adaptation module 328. Other embodiments of the vehicle experience system 310 can include additional, fewer, or different components, or can distribute functionality differently between the components. The components of the vehicle experience system 310 can include any combination of software and hardware, including, for example, programmable circuitry (e.g., one or more microprocessors), programmed with software and/or firmware, entirely in special-purpose hardwired (i.e., non-programmable) circuitry, or in a combination or such forms. Special-purpose circuitry can be in the form of, for example, one or more application-specific integrated circuits (ASICs), programmable logic devices (PLDs), field-programmable gate arrays (FPGAs), etc. In some cases, the vehicle experience system 310 includes one or more processors, such as a central processing unit (CPU), graphical processing unit (GPU), or neural processing unit (NPU), that executes instructions stored in a non-transitory computer readable storage medium, such as a memory.

The sensor abstraction component 312 receives raw sensor data from the car network 350 and/or other data sources 355 and normalizes the inputs for processing by the processing engine 330. The sensor abstraction component 312 may be adaptable to multiple vehicle models and can be readily updated as new sensors are made available.

The output module 314 generates output signals and sends the signals to the car network 365 or other data sources 360 to control electrical components of the vehicle. The output module 314 can receive a state of the vehicle and determine an output to control at least one component of the vehicle to change the state. In some embodiments, the output module 314 includes a rules engine that applies one or more rules to the vehicle state and determines, based on the rules, one or more outputs to change the vehicle state. For example, if the vehicle state is drowsiness of the driver, the rules may cause the output module to generate output signals to reduce the temperature in the vehicle, change the radio to a predefined energetic station, and increase the volume of the radio.

The connectivity adapter 316a-b enables communication between the vehicle experience system 310 and external storage devices or processing systems. The connectivity adapter 316a-b can enable the vehicle experience system 310 to be updated remotely to provide improved capability and to help improve the vehicle state detection models applied by the processing engine. The connectivity adapter 316a-b can also enable the vehicle experience system 310 to output vehicle or user data to a remote storage device or processing system. For example, the vehicle or user data can be output to allow a system to analyze for insights or monetization opportunities from the vehicle population. In some embodiments, the connectivity adapter can interface between the vehicle experience system 310 and wireless network capabilities in the vehicle. Data transmission to or from the connectivity adapter can be restricted by rules, such as limits on specific hours of the day when data can be transmitted or maximum data transfer size. The connectivity adapter may also include multi-modal support for different wireless methods (e.g., 5G or WiFi).

The user profile module 318 manages profile data of a user of the vehicle (such as a driver). Because the automotive experience generated by the vehicle experience system 310 can be highly personalized for each individual user in some implementations, the user profile module generates and maintains a unique profile for the user. The user profile module can encrypt the profile data for storage. The data stored by the user profile module may not be accessible over the air. In some embodiments, the user profile module maintains a profile for any regular driver of a car, and may additionally maintain a profile for a passenger of the car (such as a front seat passenger). In other embodiments, the user profile module 318 accesses a user profile, for example from the remote server 120, when a user enters the vehicle 110.

The settings module 320 improves the flexibility of system customizations that enable the vehicle experience system 310 to be implemented on a variety of vehicle platforms. The settings module can store configuration settings that streamline client integration, reducing an amount of time to implement the system in a new vehicle. The configuration settings also can be used to update the vehicle during its lifecycle, to help improve with new technology, or keep current with any government regulations or standards that change after vehicle production. The configuration settings stored by the settings module can be allowed locally through a dealership update or remotely using a remote campaign management program to update vehicles over the air.

The security layer 322 manages data security for the vehicle experience system 310. In some embodiments, the security layer encrypts data for storage locally on the vehicle and when sent over the air to deter malicious attempts to extract private information. Individual anonymization and obscuration can be implemented to separate personal details as needed. The security and privacy policies employed by the security layer can be configurable to update the vehicle experience system 310 for compliance with changing government or industry regulations.

In some embodiments, the security layer 322 implements a privacy policy. The privacy policy can include rules specifying types of data that can or cannot be transmitted to the remote server 120 for processing. For example, the privacy policy may include a rule specifying that all data is to be processed locally, or a rule specifying that some types of intermediate data scrubbed of personally identifiable information can be transmitted to the remote server 120. The privacy policy can, in some implementations, be configured by an owner of the vehicle 110. For example, the owner can select a high privacy level (where all data is processed locally), a low privacy level with enhanced functionality (where data is processed at the remote server 120), or one or more intermediate privacy levels (where some data is processed locally and some is processed remotely).

Alternatively, the privacy policy can be associated with one or more privacy profiles defined for the vehicle 110, a passenger in the vehicle, or a combination of passengers in the vehicle, where each privacy profile can include different rules. In some implementations, where for example a passenger is associated with a profile that is ported to different vehicles or environment, the passenger's profile can specify the privacy rules that are applied dynamically by the security layer 322 when the passenger is in the vehicle 110 or environment. When the passenger exits the vehicle and a new passenger enters, the security layer 322 retrieves and applies the privacy policy of the new passenger.

The rules in the privacy policy can specify different privacy levels that apply under different conditions. For example, a privacy policy can include a low privacy level that applies when a passenger is alone in a vehicle and a high privacy level that applies when the passenger is not alone in the vehicle. Similarly, a privacy policy can include a high privacy level that applies if the passenger is in the vehicle with a designated other person (such as a child, boss, or client) and a low privacy level that applies if the passenger is in the vehicle with any person other than the designated person. The rules in the privacy policy, including the privacy levels and when they apply, may be configurable by the associated passenger. In some cases, the vehicle experience system 310 can automatically generate the rules based on analysis of the passenger's habits, such as by using pattern tracking to identify that the passenger changes the privacy level when in a vehicle with a designated other person.

The OTA update module 324 enables remote updates to the vehicle experience system 310. In some embodiments, the vehicle experience system 310 can be updated in at least two ways. One method is a configuration file update that adjusts system parameters and rules. The second method is to replace some or all of firmware associated with the system to update the software as a modular component to host vehicle device.

The processing engine 330 processes sensor data and determines a state of the vehicle. The vehicle state can include any information about the vehicle itself, the driver, or a passenger in the vehicle. For example, the state can include an emotion of the driver, an emotion of the passenger, or a safety concern (e.g., due to road or traffic conditions, the driver's attentiveness or emotion, or other factors). As shown in FIG. 1, the processing engine can include a sensor fusion module, a personalized data processing module, and a machine learning adaptation module.

The sensor fusion module 326 receives normalized sensor inputs from the sensor abstraction component 312 and performs pre-processing on the normalized data. This pre-processing can include, for example, performing data alignment or filtering the sensor data. Depending on the type of data, the pre-processing can include more sophisticated processing and analysis of the data. For example, the sensor fusion module 326 may generate a spectrum analysis of voice data received via a microphone in the vehicle (e.g., by performing a Fourier transform), determining frequency components in the voice data and coefficients that indicate respective magnitudes of the detected frequencies. As another example, the sensor fusion module may perform image recognition processes on camera data to, for example, determine the position of the driver's head with respect to the vehicle or to analyze an expression on the driver's face.

The personalized data processing module 330 applies a model to the sensor data to determine the state of the vehicle. The model can include any of a variety of classifiers, neural networks, or other machine learning or statistical models enabling the personalized data processing module to determine the vehicle's state based on the sensor data. Once the vehicle state has been determined, the personalized data processing module can apply one or more models to select vehicle outputs to change the state of the vehicle. For example, the models can map the vehicle state to one or more outputs that, when effected, will cause the vehicle state to change in a desired manner.

The machine learning adaptation module 328 continuously learns about the user of the vehicle as more data is ingested over time. The machine learning adaptation module may receive feedback indicating the user's response to the vehicle experience system 310 outputs and use the feedback to continuously improve the models applied by the personalized data processing module. For example, the machine learning adaptation module 328 may continuously receive determinations of the vehicle state. The machine learning adaptation module can use changes in the determined vehicle state, along with indications of the vehicle experience system 310 outputs, as training data to continuously train the models applied by the personalized data processing module.

Figure 4:
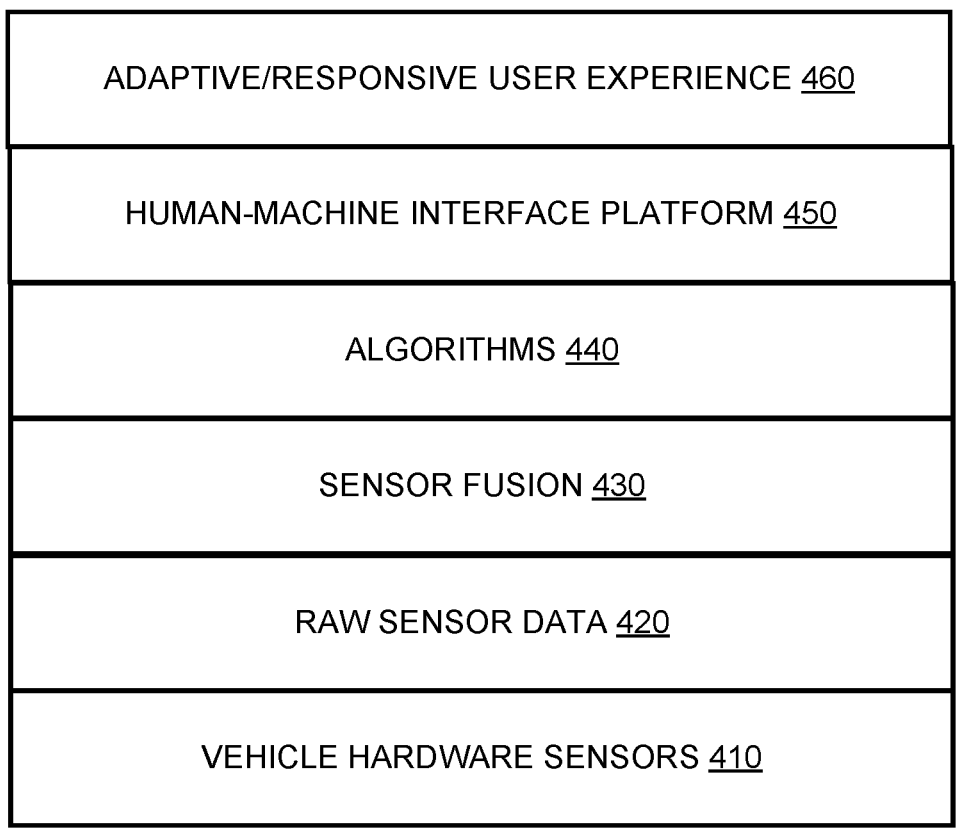
FIG. 4 is an example abstraction illustrating relationships between components and data associated with the vehicle.

FIG. 4 is an example abstraction illustrating relationships between components and data associated with the vehicle 110. As shown in FIG. 4, the vehicle 110 can be represented as a series of layers including a vehicle hardware sensor layer 410, a raw sensor data layer 420, a sensor fusion layer 430, an algorithm layer 440, a human-machine interface platform layer 450, and an adaptive/responsive user experience layer 460. The base layer of the vehicle abstraction includes vehicle sensors 410, which are hardware components that output analog or digital signals representing parameters of the vehicle 110, a context of the vehicle 110, or a state of a passenger in the vehicle. The sensor data layer 420 represents initial processing of the signals into data types or signals that are usable by various processing components of the vehicle 110 or remote server 120. For example, the sensor data layer 420 represents normalized or filtered data corresponding to the raw signals received from the sensors 215. The sensor fusion layer 430 represents a fusion of the sensor data 420, or an aggregation of the sensor data associated with multiple sensors 215 and collective analysis of this aggregated sensor data to generate parameters for personalization or control of the vehicle 110. The human-machine interface layer 450 represents interactions between a passenger in the vehicle 110 and the components of the vehicle 110. These interactions can include, for example, any content that the vehicle outputs to the passenger (such as media content, navigational content, or requests for instructions) and any inputs by the passenger into the vehicle. The interactions in the human-machine interface layer 450 can further include parameters applied by the vehicle 110 to components interacted with by the passenger, such as comfort settings or safety parameters implemented automatically by the vehicle 110. The experience layer 460 represents an overall experience of the passenger in the vehicle 110, based on the collective interactions represented by the human-machine interface layer 450.

Figure 5:
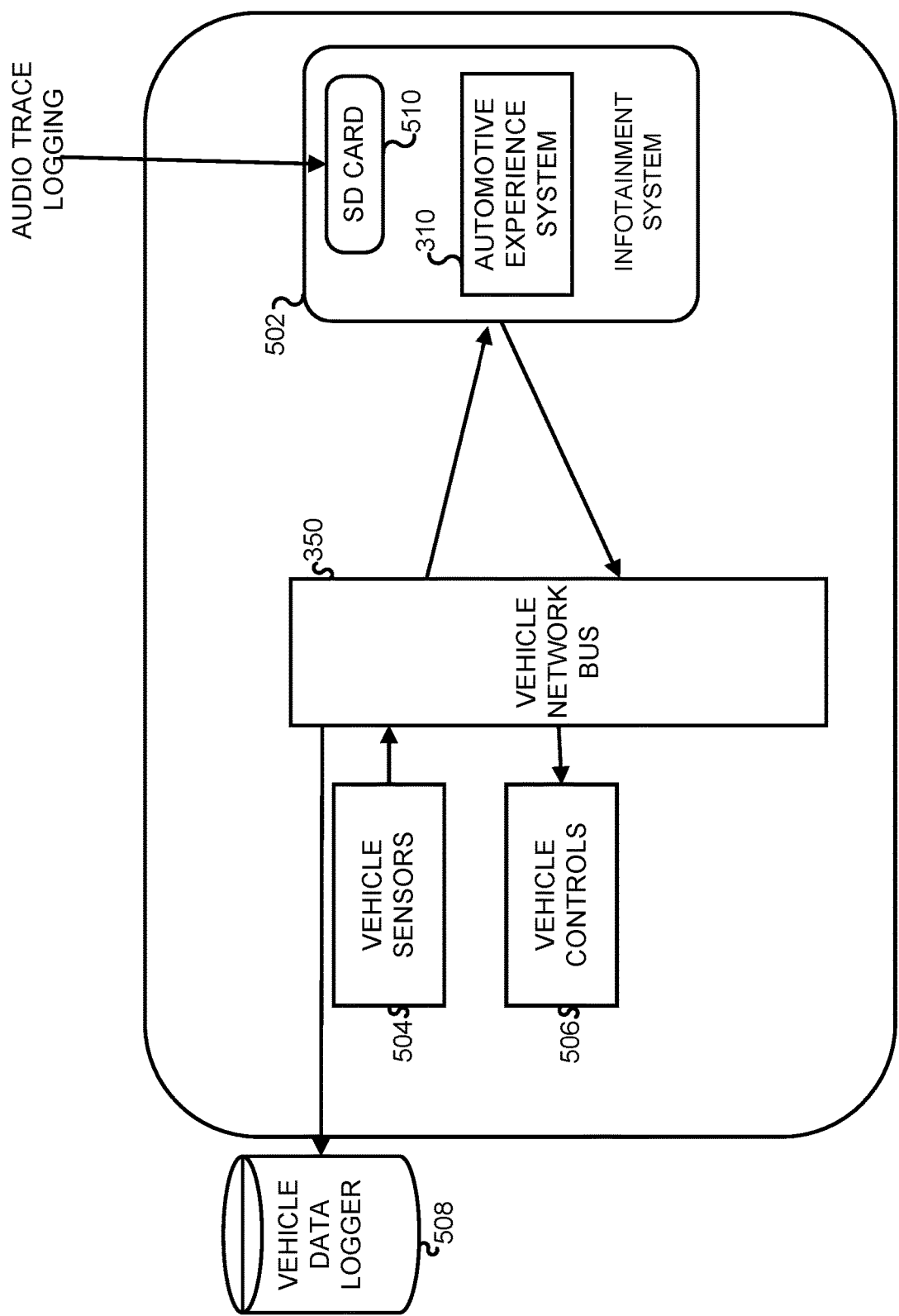
FIG. 5 is a block diagram illustrating an example configuration of the vehicle experience system with respect to other components of the vehicle.

FIG. 5 is a block diagram illustrating an example configuration of the vehicle experience system with respect to other components of the vehicle.

The infotainment system 502, along with vehicle sensors 504 and vehicle controls 506, can communicate with other electrical components of the vehicle over the car network 350. The vehicle sensors 504 can include some or all of the sensors 215 described with respect to FIG. 2, or can include different sensors. The vehicle controls 506 can control various components of the vehicle. For example, the vehicle controls 506 can include the entertainment system 210, the comfort system 225, and/or safety controls or systems in the vehicle. A vehicle data logger 508 may store data read from the car network bus 350, for example for operation of the vehicle. In some embodiments, the infotainment system 502 can also include a storage device 510, such as an SD card, to store data related to the infotainment system, such as audio logs, phone contacts, or favorite addresses for a navigation system. The infotainment system 502 can include an automotive system 310 that can be utilized to increase user experience in the vehicle.

Although FIG. 5 shows that the vehicle experience system 310 may be integrated into the vehicle infotainment system in some cases, other embodiments of the vehicle experience system 310 may be implemented using standalone hardware. For example, one or more processors, storage devices, or other computer hardware can be added to the vehicle and communicatively coupled to the vehicle network bus, where some or all functionality of the vehicle experience system 310 can be implemented on the added hardware.

Emotion Detection

Figure 6A:
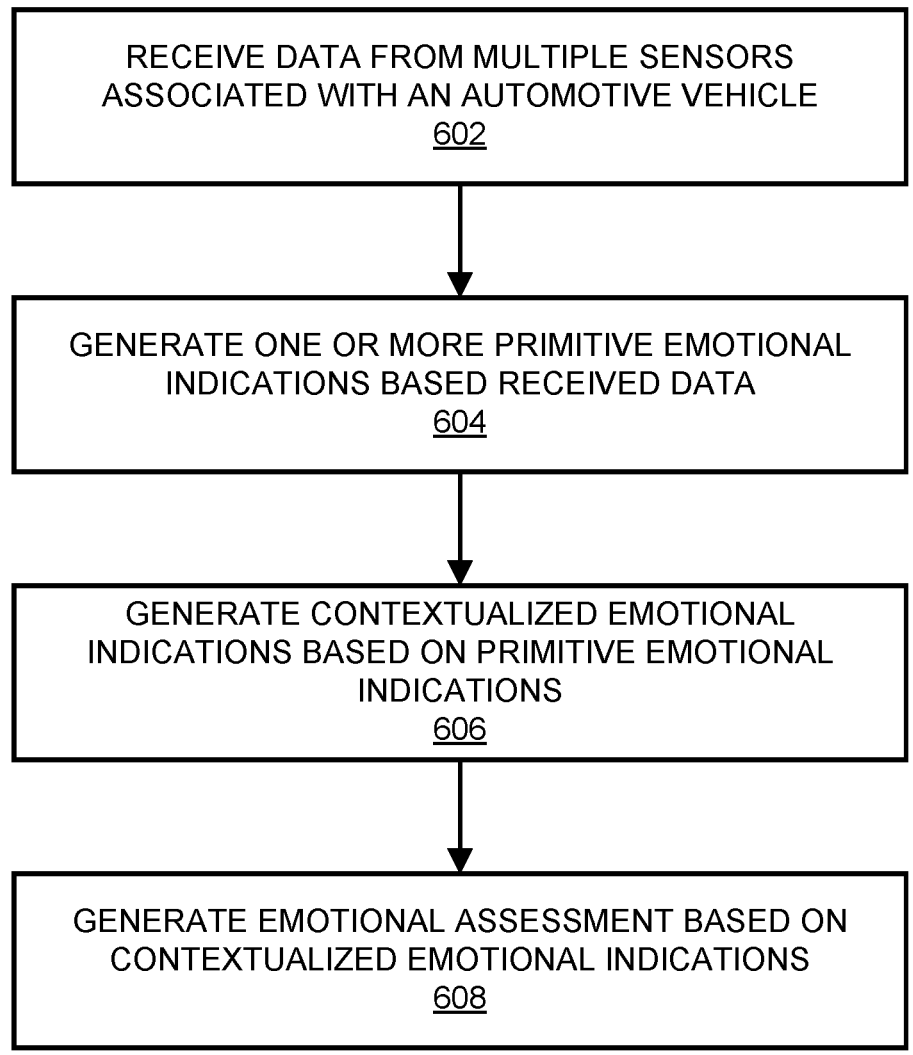
FIG. 6A is a flowchart illustrating a process to determine the driver's emotional state.
Figure 6B:
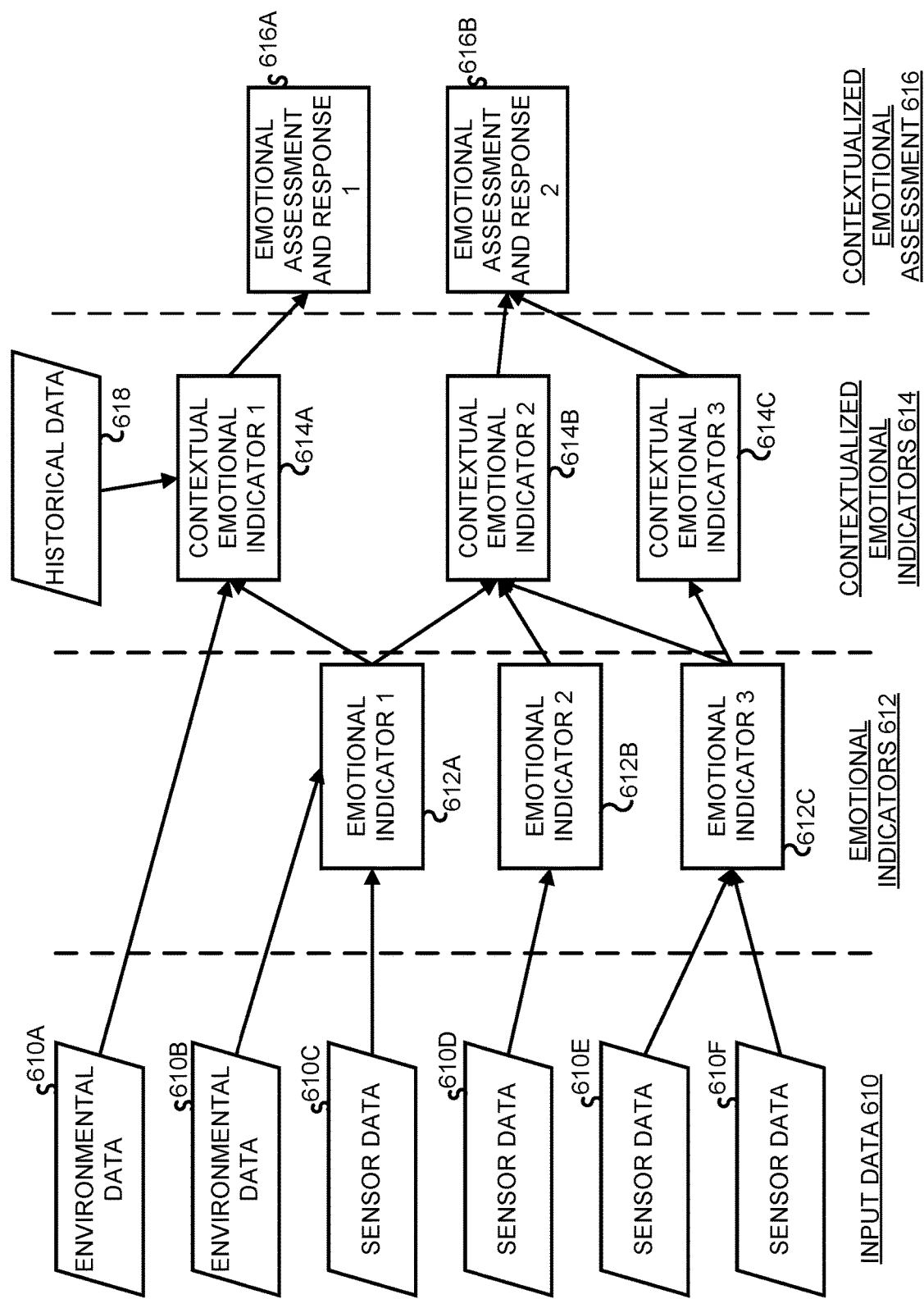
FIG. 6B illustrates example data types detected and generated during the process shown in FIG. 6A.

FIG. 6A is a flowchart illustrating a process to determine the driver's emotional state, and FIG. 6B illustrates example data types detected and generated during the process shown in FIG. 6A. The processing in FIG. 6A is described, by way of example, as being performed by the vehicle experience system 310. However, in other embodiments, other components of the vehicle 110 or the remote server 120 can perform some or all of the analysis shown in FIG. 6A.

As shown in FIG. 6A, the vehicle experience system 310 can receive, at step 602, data from multiple sensors associated with an automotive vehicle. In addition to the sensor data, the vehicle experience system 310 may receive environmental data indicating, for example, weather or traffic conditions measured by systems other than the vehicle experience system 310 or the sensors associated with the vehicle. FIG. 6B shows, by way of example, four types of sensor data and two types of environmental data that can be received at step 602. However, additional or fewer data streams can be received by the vehicle experience system 310.

As shown in FIG. 6B, the types of environmental data can include input data 610, emotional indicators 612, contextualized emotional indicators 614, and contextual emotional assessment 616. The input data 610 can include environmental data 610*a-b* and sensor data 610*c-f*. The emotional indicators 612 can include indicators 612*a-c*. The contextual emotional indicators 614 can include indicators 614*a-c*. In some cases, the contextual emotional indicators 614*a-c* can be modified based on historical data 618. The contextualized emotional assessments 616 can include various emotional assessments and responses 616*a-b*.

The vehicle experience system 310 generates, at step 604, one or more primitive emotional indications based on the received sensor (and optionally environmental) data. The primitive emotional indications may be generated by applying a set of rules to the received data. When applied, each rule can cause the vehicle experience system 310 to determine that a primitive emotional indication exists if a criterion associated with the rule is satisfied by the sensor data. Each rule may be satisfied by data from a single sensor or by data from multiple sensors.

As an example of generating a primitive emotional indication based on data from a single sensor, a primitive emotional indication determined at step 604 may be a classification of a timbre of the driver's voice into soprano, mezzo, alto, tenor, or bass. To determine the timbre, the vehicle experience system 310 can analyze the frequency content of voice data received from a microphone in the vehicle. For example, the vehicle experience system 310 can generate a spectrum analysis identify various frequency components in the voice data. A rule can classify the voice as soprano if the frequency data satisfies a first condition or set of conditions, such as having certain specified frequencies represented in the voice data or having at least threshold magnitudes at specified frequencies. The rule can classify the voice as mezzo, alto, tenor, or bass if the voice data instead satisfies a set of conditions respectively associated with each category.

As an example of generating a primitive emotional indication based on data from multiple sensors, a primitive emotional indication determined at step 604 may be a body position of the driver. The body position can be determined based on data received from a camera and one or more weight sensors in the driver's seat. For example, the driver can be determined to be sitting up straight if the camera data indicates that the driver's head is at a certain vertical position and the weight sensor data indicates that the driver's weight is approximately centered and evenly distributed on the seat. The driver can instead be determined to be slouching based on the same weight sensor data, but with camera data indicating that the driver's head is at a lower vertical position.

The vehicle experience system 310 may determine the primitive emotional indications in manners other than by the application of the set of rules. For example, the vehicle experience system 310 may apply the sensor and/or environmental data to one or more trained models, such as a classifier that outputs the indications based on the data from one or more sensors or external data sources. Each model may take all sensor data and environmental data as inputs to determine the primitive emotional indications or may take a subset of the data streams. For example, the vehicle experience system 310 may apply a different model for determining each of several types of primitive emotional indications, where each model may receive data from one or more sensors or external sources.

Example primitive emotional indicators that may be generated by the media selection module 220, as well as the sensor data used by the module to generate the indicators, are as follows:

| Primitive Emotional Indicator | Description | Sensor Needed |
|---|---|---|
| Voice | | |
| Timbre | Unique Overtones and frequency of the voice. Categorized as: Soprano Mezzo Alto Tenor Bass | Microphone |
| Decibel Level | Absolute decibel level of the human voice detected. | Microphone |
| Pace | The cadence at which the subject is speaking | Microphone |
| Facial | | |
| Anger | The detection that the occupant is angry and unhappy with something | Front Facing Camera |
| Disgust | The response from a subject of distaste or displeasure | Front Facing Camera |
| Happiness | Happy and general reaction of pleasure | Front Facing Camera |
| Sadness | Unhappy or sad response | Front Facing Camera |
| Surprise | Unexpected situation | Front Facing Camera |
| Neutral | No specific emotional response. | Front Facing Camera |
| Body | | |
| Force of Touch | The level of pressure applied to the Entertainment screen with a user interaction | Entertainment/ Infotainment screen |
| Body Position | The position of the subject body, detected by computer vision in combination with the seat sensors and captured in X, Y, Z coordinates | Camera + Occupant Weight Sensor |

Based on the primitive emotional indications (and optionally also based on the sensor data, the environmental data, or historical data associated with the user), the vehicle experience system 310 generates, at step 606, contextualized emotional indications. Each contextualized emotional indication can be generated based on multiple types of data, such as one or more primitive emotional indications, one or more types of raw sensor or environmental data, or one or more pieces of historical data. By basing the contextualized emotional indications on multiple types of data, the vehicle experience system 310 can more accurately identify the driver's emotional state and, in some cases, the reason for the emotional state.

In some embodiments, the contextualized emotional indications can be determined by applying a set of rules to the primitive indications. For example, the vehicle experience system 310 may determine that contextual emotional indication 2 shown in FIG. 6B exists if the system detected primitive emotional indications 1, 2, and 3. Below is an example emotional indication model including rules that can be applied by the vehicle experience system 310:

Happy:
  Event Detected: Mouth changes shape, corners turn upwards, timbre of voice moves up half an octave
  Classification: Smile
  Contextualization: Weather is good, traffic eases up
  Verification: Positive valence Output/Action: Driver is happy, system proposes choices to driver based on ambience, music, driving style, climate control, follow-up activities, linked activities, driving route, suggestions, alternative appointment planning, continuous self-learning, seat position, creating individualized routines for relaxation or destressing.

In other cases, the contextualized emotional indications can be determined by applying a trained model, such as a neural network or classifier, to multiple types of data. For example, primitive emotional indication 1 shown in FIG. 6A may be a determination that the driver is happy. The vehicle experience system 310 can generate contextualized emotional indication 1—a determination that the driver is happy because the weather is good and traffic is light—by applying primitive emotional indication 1 and environmental data (such as weather and traffic data) to a classifier. The classifier can be trained based on historical data, indicating for example that the driver tends to be happy when the weather is good and traffic is light, versus being angry, frustrated, or sad when it is raining or traffic is heavy. In some cases, the model is trained using explicit feedback provided by the passenger. For example, if the vehicle experience system 310 determines based on sensor data that a person is stressed, the vehicle experience system 310 may ask the person "You appear to be stressed; is that true?" The person's answer to the question can be used as an affirmative label to retrain and improve the model for better determination of the contextualized emotional indications.

The contextualized emotional indications can include a determination of a reason causing the driver to exhibit the primitive emotional indications. For example, different contextualized emotional indications can be generated at a different times based on the same primitive emotional indication with different environmental and/or historical data. For example, as discussed above, the vehicle experience system 310 may identify a primitive emotional indication of happiness and a first contextualized emotional indication indicating that the driver is happy because the weather is good and traffic is light. At a different time, the vehicle experience system 310 may identify a second contextualized emotional indication based on the same primitive emotional indication (happiness), which indicates that the driver is happy in spite of bad weather or heavy traffic as a result of the music that is playing in the vehicle. In this case, the second contextualized emotional indication may be a determination that the driver is happy because she enjoys the music.

Finally, at step 608, the vehicle experience system 310 can use the contextualized emotional indications to generate or recommend one or more emotional assessment and response plans. The emotional assessment and response plans may be designed to enhance the driver's current emotional state (as indicated by one or more contextualized emotional indications), mitigate the emotional state, or change the emotional state. For example, if the contextualized emotional indication indicates that the driver is happy because she enjoys the music that is playing in the vehicle, the vehicle experience system 310 can select additional songs similar to the song that the driver enjoyed to ensure that the driver remains happy. As another example, if the driver is currently frustrated due to heavy traffic but the vehicle experience system 310 has determined (based on historical data) that the driver will become happier if certain music is played, the vehicle experience system 310 can play this music to change the driver's emotional state from frustration to happiness.

Below are example scenarios and corresponding corrective responses that can be generated by the vehicle experience system 310:

| Contextualized Emotional Scenario | Description | Primitive Emotional Indicators and Sensors | Personalized Corrective Response |
|---|---|---|---|
| Safety | | | |
| Road Rage | The personalized assessment that a driver is aggravated to the point that their actions could harm themselves or others. This assessment will take into consideration the history of the specific user and have a personalized threshold it will learn overtime | Vehicle Power Train - Speed, Acceleration External - Traffic, weather Emotional Indicators of Anger and Disgust Body Position Deltas - Physical Agitation | Audio and visual warning for driver to be aware of situation. Massage activated on seat. Temperature reduced in vehicle Mood lighting adjusted to be less upsetting (no red) |
| Entertainment | | | |
| Head Bop | The physical reaction a subject has while listening to a media source. This goes beyond simple enjoyment, to the mode of physical reaction the user demonstrates. This can be parameterized as Metal, Sway, Pop. | Front Facing Camera (Facial changes, mouthing words) Body Position (Delta) Cabin Microphone (music bpm, key signature) Entertainment Media Metadata (song, artist, timestamp, volume change) | None - Captured Data Point to be used for analysis or joined with other data for behavioral analysis and/or monetization purposes |
| Comfort | | | |
| Emotional Stability | This feature will assess the desired emotional state of the occupant, and adjust the environment to maintain that state for the subject. The requested state will be requested by the user, and can be Calm, Sad, Intense or Happy. | Front Facing Camera Body Position (Delta) Cabin Microphone Infotainment Status | Change of Audio Station Massage activated on seat. Cabin temperature adjusted in vehicle Mood lighting adjustments Seat temperature |

The following table illustrates other example state changes that can be achieved by the vehicle experience system 310, including the data inputs used to determine a current state, an interpretation of the data, and outputs that can be generated to change the state.

| Emotional Scenario | Data Input | System Interpretation | Output |
|---|---|---|---|
| Stress Reduction | Driver Monitoring Camera<br>Analog Microphone Signal<br>DSP: Music beat detection<br>DSP: Processed audio<br>CAN Data: Speed<br>CAN Data: Acceleration<br>CAN Data: In-cabin decibel level<br>External data: Traffic conditions<br>External data: Weather condition | Facial Coding analysis<br>Voice frequency detection<br>Breathing patterns<br>Deviation from historical user behavior<br>Intensity of acceleration<br>Anomaly detection from norm<br>Pupils dilated<br>Posture recognition<br>Gesture detection<br>Restlessness detection | Alternative Route Suggestions<br>Interactive spoken prompts to driver<br>Enhanced proactive communication regarding uncontrollable stress factors: weather, traffic conditions, location of fueling and rest areas, etc.<br>Activation of adaptive cruise control (ACC)<br>Activation of Lane Assist<br>Modify the light experience<br>Air purification activated<br>Regulate the sound level<br>Aromatherapy activation<br>Dynamic audio volume modification<br>Dynamic drive mode adjustment<br>Activate seat massage<br>Adjust seat position |
| Music Enjoyment | Driver Monitoring Camera<br>Analog Microphone Signal<br>DSP: Music beat detection<br>DSP: In-Cabin Decibel Level<br>CAN Data: Humidity Detection<br>CAN Data: Acceleration<br>CAN Data: Increase in volume level<br>CAN Data: Audio screen in MMI<br>External data: Traffic conditions<br>External data: Weather conditions | Posture recognition<br>Gesture detection<br>Voice frequency detection<br>Facial expression change<br>Zonal determination of music enjoyment<br>Facial Expression determination<br>Voice frequency detection<br>Upper body pose estimation<br>Correlation to past user behavior<br>Detect audio key signature<br>Intensity of acceleration | Lighting becomes dynamically reactive to music<br>All driver assist functions activated (e.g. ACC, Lane Assist)<br>Dynamically-generated music recommendations designed for the specific length of the journey<br>Deactivate seat massage<br>Lower temperature based on increased movement and humidity<br>Dynamic drive mode adjustment to comfort mode<br>When car stopped, Karaoke Mode activated |
| Road Rage Abatement | External data: Traffic conditions<br>Driver Monitoring Camera<br>Analog Microphone Signal<br>DSP: Processed Audio Signal<br>CAN Data: Audio volume level<br>CAN Data: Distance to car ahead<br>CAN Data: Lane position<br>CAN Data: Speed<br>CAN Data: Acceleration<br>CAN Data: In-cabin decibel level<br>External data: Weather conditions<br>DSP: External noise pollution<br>CAN Data: Force touch detection<br>CAN Data: Steering wheel angle<br>Body seating position<br>CAN Data: Passenger seating location | Upper body pose<br>Facial Expression determination<br>Voice frequency detection<br>Breathing patterns<br>Deviation from historical user behavior<br>Intensity of acceleration<br>Check for erratic driving<br>Anomaly detection from norm<br>Pupils dilated<br>Posture recognition<br>Gesture detection<br>Restlessness detection<br>Steering style<br>Restlessness | Alternative Route Suggestions<br>Interactive spoken prompts to driver<br>Explain through simple language the contributing stress factors: Enhanced proactive communication regarding uncontrollable stress factors: weather, traffic conditions, location of fueling and rest areas, etc.<br>Activation of ACC<br>Activation of Lane Assist<br>Modify the light experience<br>Regulate the sound level<br>Air purification activated<br>Aromatherapy activation<br>Dynamic audio volume modification<br>Dynamic drive mode adjustment<br>Activate seat massage<br>Adjust seat position<br>Adjust to average user comfort setting |

-continued

| Emotional Scenario | Data Input | System Interpretation | Output |
|---|---|---|---|
| Tech Detox | Driver Monitoring Camera<br>Analog Microphone Signal<br>Cobalt DSP: In-Cabin Decibel Level<br>CAN Data: Ambient Light Sensor<br>CAN Data: Infotainment Force Touch<br>CAN Data: Decrease in volume level<br>CAN Data: Audio screen in infotainment system<br>External data: Traffic conditions<br>External data: Weather condition | Facial stress detection<br>Voice frequency changes<br>Breathing patterns<br>Slow response to factors<br>Pupils dilated<br>Posture recognition<br>Gesture detection<br>Color temperature of in-vehicle lights<br>Correlation with weather | Countermeasures<br>Scent<br>Music<br>Alternative Route Suggestions<br>Spoken Acceleration- Air purification activated<br>Activation of security system<br>Proactive communication regarding weather, traffic conditions, rest areas, etc.<br>Dynamic drive mode adjustment |
| Do Not Disturb | CAN Data: Passenger seating location<br>Body seating position<br>Driver Monitoring Camera<br>Analog Microphone Signal<br>DSP: Processed Audio Signal<br>CAN Data: Audio volume level<br>CAN Data: Drive mode: comfort<br>CAN Data: In-cabin decibel level<br>CAN Data: Day and Time<br>External data: Weather conditions<br>DSP: External noise pollution | Rate of change against expected norm<br>Frequency<br>Intensity<br>Delta of detected events from typical status | Countermeasures<br>Scent<br>Music<br>Alternative Route Suggestion<br>Spoken Acceleration<br>Activation of security system<br>Proactive communication regarding weather, traffic conditions, rest areas, etc.<br>Dynamic drive mode adjustment |
| Drowsiness | Driver Monitoring Camera<br>Body seating position<br>Analog Microphone Signal<br>DSP: Processed Audio Signal<br>CAN Data: Steering Angle<br>CAN Data: Lane departure<br>CAN Data: Duration of journey<br>CAN Data: Day and Time<br>CAN Data: Road Profile Estimation<br>External data: Weather conditions<br>CAN Data: Audio level | Zonal detection<br>Blink detection<br>Drive Style<br>Steering Style<br>Rate of change against expected norm<br>Frequency<br>Intensity<br>Delta of detected event from typical status | Countermeasures<br>Scent<br>Music<br>Alternative Route Suggestions<br>Spoken Acceleration - Air purification activated<br>Activation of security systems<br>Proactive communication regarding weather, traffic conditions, rest areas, etc.<br>"Shall I open the windows?"<br>Dynamic drive mode adjustment<br>Significant cooling of interior cabin temperature<br>Adapting driving mode to auto mode (detect the bumpy road) |
| Driver Distraction | Driver Monitoring Camera<br>Analog Microphone Signal<br>DSP: Vocal frequency<br>DSP: Processed audio<br>CAN Data: Lane departure<br>CAN Data: MMI Force Touch<br>CAN Data: In-cabin decibel level<br>CAN Data: Mobile phone notification and call information | Rate of change against expected norm<br>Frequency<br>Intensity<br>Delta of detected events from typical status | Countermeasures<br>Scent<br>Music<br>Alternative Route Suggestions<br>Spoken Acceleration<br>Activation of security systems<br>Proactive communication regarding weather, traffic conditions, rest areas, etc.<br>Dynamic drive mode adjustment |

| Emotional Scenario | Data Input | System Interpretation | Output |
|---|---|---|---|
| | External data: Traffic conditions External data: Weather condition | | |

Current implementations of emotion technology suffer by their reliance on a classical model of Darwinian emotion measurement and classification. One example of this is the wide number of facial coding-only offerings, as facial coding on its own is not necessarily an accurate representation of emotional state. In the facial coding-only model, emotional classification is contingent upon a correlational relationship between the expression and the emotion it represents (for example: a smile always means happy). However, emotions are typically more complex. For example, a driver who is frustrated as a result of heavy traffic may smile or laugh when another vehicle cuts in front of him as an expression of his anger, rather than an expression of happiness. Embodiments of the vehicle experience system 310 take a causation-based approach to biofeedback by contextualizing each data point that paints a more robust view of emotion. These contextualized emotions enable the vehicle experience system 310 to more accurately identify the driver's actual, potentially complex emotional state, and in turn to better control outputs of the vehicle to mitigate or enhance that state.

Figure 7:
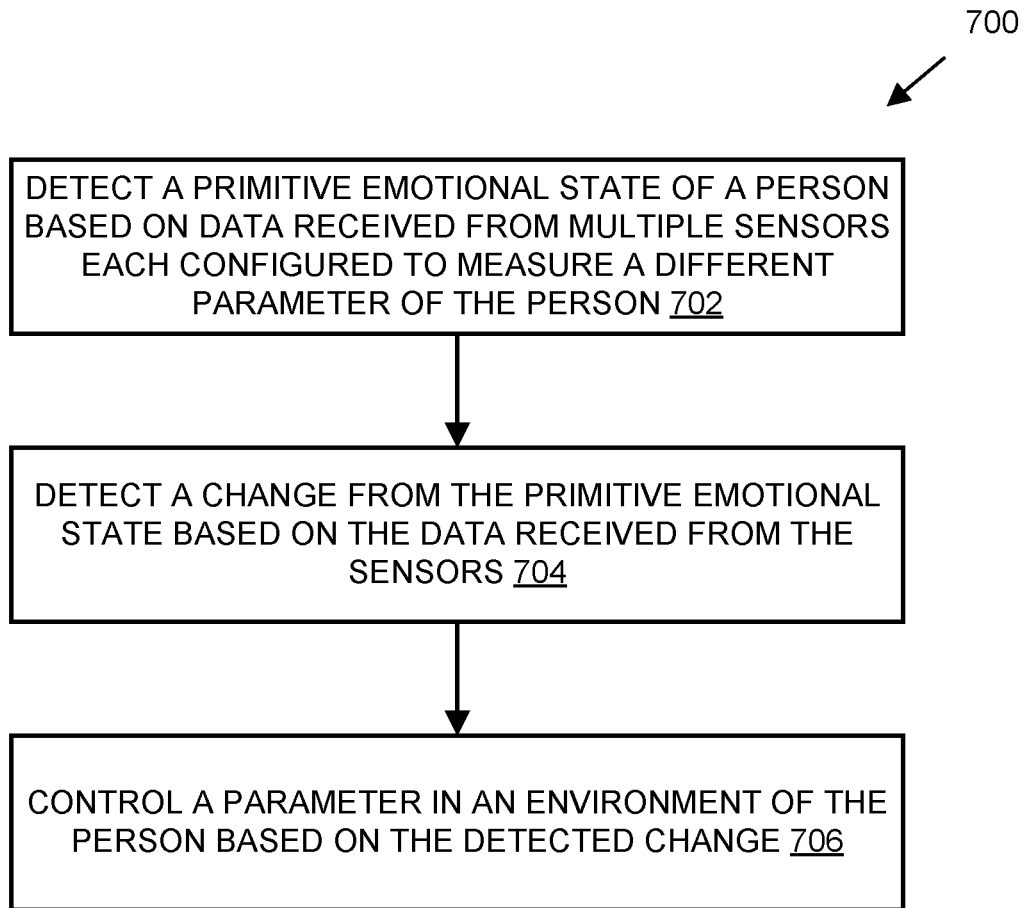
FIG. 7 is a flowchart illustrating another process for detecting an emotional state of a person, according to some embodiments.

FIG. 7 is a flowchart illustrating another process 700 for detecting an emotional state of a person, according to some embodiments. The process 700 can be performed by the vehicle experience system 310, although the process 700 is not limited to execution in a vehicle. The process 700 can represent a person's emotional state as a comparison to another emotional state. Thus, the emotional state generated by the vehicle experience system 310 using the process 700 may not include an explicit determination, for example, that a driver is stressed, but rather that the driver is exhibiting emotional indications different from those exhibited in the driver's neutral state and that cause the vehicle 110 to implement a stress mitigation response. Other embodiments of the process 700 can include additional, fewer, or different steps than those shown in FIG. 7, for example to include one or more of the steps described with respect to FIG. 6A.

As shown in FIG. 7, the vehicle experience system 310 detects, at step 702, a preliminary emotional state of a person. The preliminary emotional state can, in some cases, be an emotional state measured non-contextually at a first time. In other cases, the preliminary emotional state can be a baseline emotional state. The baseline emotional state can be determined based on data received from multiple sensors in the vehicle 110, each of which is configured to measure a different parameter of the person. The baseline emotional state can represent one or more primitive emotional indications that are determined to correspond to a neutral state of the passenger. The "neutral" state can be determined, for example, based on an amount of time the passenger exhibits the primitive emotional indications, such that a primitive emotional indication exhibited for a greatest amount of time is identified as an indication of the neutral state. Alternatively, the neutral state can be determined by identifying a time the passenger is expected to be in a neutral state, such as a time when traffic and weather are moderate. The primitive emotional indications can be generated as described with respect to FIG. 6A.

At step 704, the vehicle experience system 310 detects a change in the person's emotional state based on the data received from the sensors 215. For example, the vehicle experience system 310 detects one or more primitive emotional indications that are different than the primitive emotional indications associated with the preliminary emotional state. The detected change can, by way of example, be represented as a contextual emotional indication.

Based on the detected change in the person's emotional state, the vehicle experience system 310 controls a parameter in an environment of the person. For example, the vehicle experience system 310 can control one or more parameters of an entertainment, comfort, or safety system in the vehicle 110 based on the changed emotional state.

Personalization Overview

As noted above, various characteristics of an environment (e.g., a detected emotion of a vehicle passenger) can be obtained and one or more output actions can be performed based on the obtained characteristics. For instance, various features of a vehicle can be modified (e.g., light brightness levels can be modified) based on detecting an emotional state of a driver of a vehicle using a series of vehicle sensors. Further, the output actions can be based on user-specific information to provide a personalized user experience in the vehicle.

Figure 8:
FIG. 8 is an example flow diagram of a process for generating user-specific output actions in a vehicle.

FIG. 8 is an example flow diagram 800 of a process for generating user-specific output actions in a vehicle. As shown in FIG. 8, a process may include acquiring various user characteristic information that relates to a particular user (block 802). Examples of user characteristic information can include biometric information of a user, previous feedback information provided by the user, driving patterns and tendencies by the user, preferred vehicle settings for the user, etc. The user characteristic information can be acquired and processed to develop a profile of the user that can be utilized as a model in generating user-specific output actions.

The process can include processing user characteristic information to generate a user profile (block 804). For example, driving tendencies and patterns of the user can be processed to determine a driving profile type that corresponds to one of a series of predetermined driving profiles. As another example, the profile can include vehicle settings that are specific to the user. The profile of the user can be used to develop a model that correlates various vehicle inputs and corresponding vehicle output actions.

The process can include identifying user(s) in the vehicle (block 806). For instance, facial recognition can be used to identify a driver in a driver region of the vehicle. As another example, other biometric information (e.g., height/weight of the user) can be acquired to identify a passenger in a passenger region of the vehicle. Upon identifying the user in a region of the vehicle (e.g., driver seat, passenger seat), user characteristic information and/or a user-specific model associated with the identified user can be retrieved and/or derived.

The process can include detecting an emotion or emotional state relating to the user (block 808). The emotional state of the user may impact the resultant output action in the vehicle. Detecting an emotional state of the user may include any of the features as discussed above. As described in greater detail below, features relating to the emotional state of a user can be user-specific.

The process may include generating user-specific output actions in the vehicle (block 810). The output actions can include actions performed by components of the vehicle either interior of the vehicle or exterior of the vehicle. For instance, an output action can include playing a specific form of media (e.g., audio/video) in the vehicle, adjusting the temperature in the vehicle, modifying light settings in the vehicle, changing computer-generated directions to a destination, etc. The user-specific output actions can be based on any of the user profile for the user and the detected emotional state of the user.

As an example, a series of user characteristics (e.g., a preferred coffee order at a coffee shop, a preferred cuisine, payment information, and a destination location) can be retrieved relating to a user. Upon detecting an input event (e.g., detecting congestion on the path to an initial destination), a user profile for the user can be processed to determine that the user generally stops for coffee at the coffee shop when congestion on a road occurs. The system can also determine that an emotional state of the user is relaxed (e.g., the user does not have any meetings scheduled, the time of day is generally when the user is not busy). Responsive to determining that the user has accepted the recommended action of stopping at the coffee shop, a coffee order for the user at the coffee shop can be placed and the destination can be modified to include the location of the coffee shop. The present process may provide user-specific output actions that can increase user experience in the vehicle.

Example Method for Performing Output Actions Based on a User-Specific Profile Model In some embodiments, the present embodiments relate to generating a user-specific profile model and implementing an output action based on the user-specific profile model. The user-specific profile model may be iteratively updated to account for new information relating to user-implemented modifications to the vehicle environment. Output actions (e.g., modifications to features of the vehicle) can be generated and implemented using the user-specific profile model.

The method may include retrieving a series of predetermined profile types. Each predetermined profile type may include a series of features common among a subset of users. For example, a predetermined profile type can include a "health/fitness" profile type that includes features common among individuals that prioritize their personal health and fitness.

The method may include acquiring a stream of user characteristic data indicative of modifications to settings of a vehicle implemented by the user. For instance, the user characteristic data can include preferred internal climate settings that is implemented by the user. As another example, the user characteristic data can include a destination requested by the user at a specific time.

The method may include, for each portion of user characteristic data of the stream of user characteristic data, comparing the user characteristic data with the series of predetermined profile types to determine a first predetermined profile type with features that correspond to the user characteristic data.

In some embodiments, the method may include presenting an emotional state request to the user requesting an audio response indicative of an emotional state of the user, receiving the audio response indicative of the emotional state of the user, processing the audio response to derive the emotional state of the user, wherein the emotional state is processed with the set of vehicle environmental data using the user-specific profile model to generate an updated output action that modifies one or more vehicle features.

In some embodiments, the method may include identifying an identity of the user located within the vehicle. The user-specific profile model may be retrieved responsive to identifying the identity of the user. Identifying the identity of the user may be based on any of comparing biometric data included in the data acquired by the series of sensors with a listing of biometric data of a series of known users and receiving an identification message from a mobile device associated with the user that is indicative of the identity of the user.

The method may include, for each portion of user characteristic data of the stream of user characteristic data, modifying a user-specific profile model to include the determined features that correspond to the user characteristic data. This may personalize the user-specific profile model, as a series of features that correspond to user characteristic data are included in the user-specific profile model. The user-specific profile model can be used to generate output actions that are unique to the user.

The method may include processing a set of vehicle environmental data acquired by a series of sensors disposed on the vehicle using the modified user-specific profile model to generate an output action that modifies one or more vehicle features.

The method may include inspecting data acquired by the series of sensors disposed on the vehicle to identify an emotional state corresponding to the user.

In some embodiments, identifying the emotional state corresponding to the user further comprises inspecting the data acquired by the series of sensors to identify a deviation between a set of baseline biometric characteristics and a set of obtained biometric characteristics that is indicative of the emotional state of the user and comparing the deviation between the set of baseline biometric characteristics and the set of obtained biometric characteristics with a series of predetermined emotional states to identify a predetermined emotional state with features that correspond to the deviation between the set of baseline biometric characteristics and the set of obtained biometric characteristics.

In some embodiments, identifying the emotional state corresponding to the user further comprises retrieving a series of predetermined emotional states, each predetermined emotional state including a plurality of features indicative of an emotion, and comparing the data acquired by the series of sensors with the series of predetermined emotional states to identify a predetermined emotional state with features that correspond to the data acquired by the series of sensors, wherein the identified emotional state includes features of the predetermined emotional state.

In some embodiments, the method may include determining an operational state of the vehicle that includes an operating state and an idle state, wherein only a subset of output actions are allowed to be performed when in the operating state, determining that the operational state of the vehicle has transitioned from the idle state to the operating state, responsive to determining that the operational state of the vehicle has transitioned from the idle state to the operating state, presenting a series of recommended output actions to the user that are capable of being performed in the transitioned operational state, and performing a number of the recommended output actions responsive to obtaining a response from the user indicating a confirmation to perform the number of recommended output actions.

The method may include performing the generated output action to modify one or more features of the vehicle. In some embodiments, the method may include presenting a series of output actions capable of being performed on the vehicle to the user by processing the set of vehicle environmental data using the user-specific profile model, and receiving an indication to perform an identified output action of the series of output actions presented to the user, wherein the identified output action is performed on the vehicle.

In some embodiments, the method may include presenting a request for feedback to the user relating to the output actions performed on the vehicle, and receiving a response from the user including an indication of whether the output action performed on the vehicle was appropriate, wherein the user-specific profile model is updated to include the vehicle environment characteristics and the generated output action.

In some embodiments, the method may include determining that a routed destination of the vehicle is within a threshold distance of an external device environment associated with the user, and responsive to determining that the routed destination of the vehicle is within the threshold distance of the external device environment associated with the user, sending an indication to the external device environment including a request to perform output actions that correspond to the one or more output actions performed on the vehicle.

In some embodiments, the vehicle environment may be configured to perform steps relating to various medical applications. For instance, the series of sensors in the vehicle can acquire data relating to a user that can be utilized in diagnosing various medical conditions. As another example, the infotainment system or heads up display can initiate a video conference with a medical provider over an encrypted communication interface. The medical provider can access and review data acquired by the sensors in the vehicle to diagnose various illnesses and provide medical advice to the user in the vehicle.

Acquisition of User Characteristic Information

As described above, user characteristic information representing various features relating to the user can be acquired. A series of vehicle sensors can be utilized in capturing data that can be processed to derive user characteristic information.

One such example of user characteristic information can include driving tendencies of the user. Driving tendencies can include common tendencies of the user's driving style. For example, a type of road (e.g., dirt road, highways, gravel) and a relative speed on each type of road may be included as driving tendencies. As another example, driving tendencies can include an aggressiveness in turning the vehicle, an average speed of the vehicle at various times, average stopping times of the vehicle, an average number of passengers in the vehicle, common destinations in the vehicle, etc.

Driving tendencies can be utilized in generating a driving profile for the user, which is described in greater detail below. The driving profile can modify output actions for the user.

Another example of user characteristic information can include information relating to the user derived from a series of sensors in the vehicle. Information relating to the user can include desired vehicle settings (e.g., seat position, vehicle temperature, light brightness settings), user-specific emotional state characteristics (e.g., a heartbeat of the user, a gaze of the user), etc.

The user characteristic information can be retrieved from third-party sources. For instance, information gathered from social media applications, a smart home environment, sensor data from a previously-occupied vehicle by the user, etc.

In some embodiments, user characteristic information may be updated based on feedback provided by the user. For example, upon modifying a temperature of the vehicle, the system can prompt the user to indicate whether the modified temperature is preferable to the user. The response provided by the user can be indicative of whether the user prefers the modified temperature or not.

The user characteristic information can include media settings, such as video/audio playback settings, volume controls, etc. For instance, if a user pauses a video playing on a display, the time position of the video when it was paused can be stored and associated with the user. Accordingly, when the user wants to continue playback of the vide, the system can retrieve the time position of the video when it was paused and resume play at that time position.

The user characteristic information can be formatted in a specific format and maintained locally and/or remotely by computing resources in the computing environment as described herein. For instance, database(s) can sort various user characteristic information types for the user such that the user characteristic information can be retrieved for further processing.

User Profile Generation

A user profile for a user can be generated based on the user characteristic information. A user profile can include a model that can be utilized in personalizing output actions and recommended output actions for a user in the vehicle. For instance, the user profile can be indicative of driving tendencies and/or desired vehicle settings for a user.

In some embodiments, a user can initially include a default user profile. The default user profile can include a universal series of characteristics that correspond to default settings for users. For instance, the default user profile can include a neutral set of settings that correspond to an average user of a vehicle. In many cases, the default user profile can be geographically-specific, i.e. the default user profile can be modified based on a location of the vehicle. For example, a first default user profile in an urban location may include settings that correspond to drivers of the vehicle commuting on highways and urban roads. Additionally, a second default profile in a rural location can include different settings that generally correspond to drivers of vehicles that operate the vehicles off-road or in various driving conditions. The default user profile can be iteratively modified to be a user-specific profile based on continuously obtaining more information relating to the user.

Generating the user profile can include identifying one of a series of profile types that corresponds to the user characteristic information. A profile type in the series of profile types can include a set of common characteristics that is common to a plurality of users. For example, a profile type can include a "car enthusiast" type that includes commonly associated features relating to users that generally have positive interactions with performance features of the vehicle (e.g., driving off-road, driving at higher speeds). As another example, a profile type can include an "executive"

type that includes commonly associated features relating to users that generally have positive interactions with business-related features of the vehicle (e.g., identifying meetings on a synchronized calendar, identifying routes to a destination that have a lowest drive time).

As more user characteristic information is gathered, pattern matching may be used to match characteristics in the user characteristic information with features included in the series of profile types. For instance, identifying that the user is driving the vehicle in congested areas can match features of an "executive" profile type that relates to users that commonly drive in congested areas. As another example identifying that the user frequently enables power-saving settings in the vehicle may match features with a "eco-friendly" profile type that relates to users that commonly attempt to energy-efficiency of the vehicle.

In some embodiments, a user profile can be generated that is unique to the user. For instance, various aspects of each of the series of profile types can be incorporated into a new profile for the user. For example, as features are matched with a profile type, the matched feature of the profile type can be incorporated into the new profile for the user.

Figure 9:
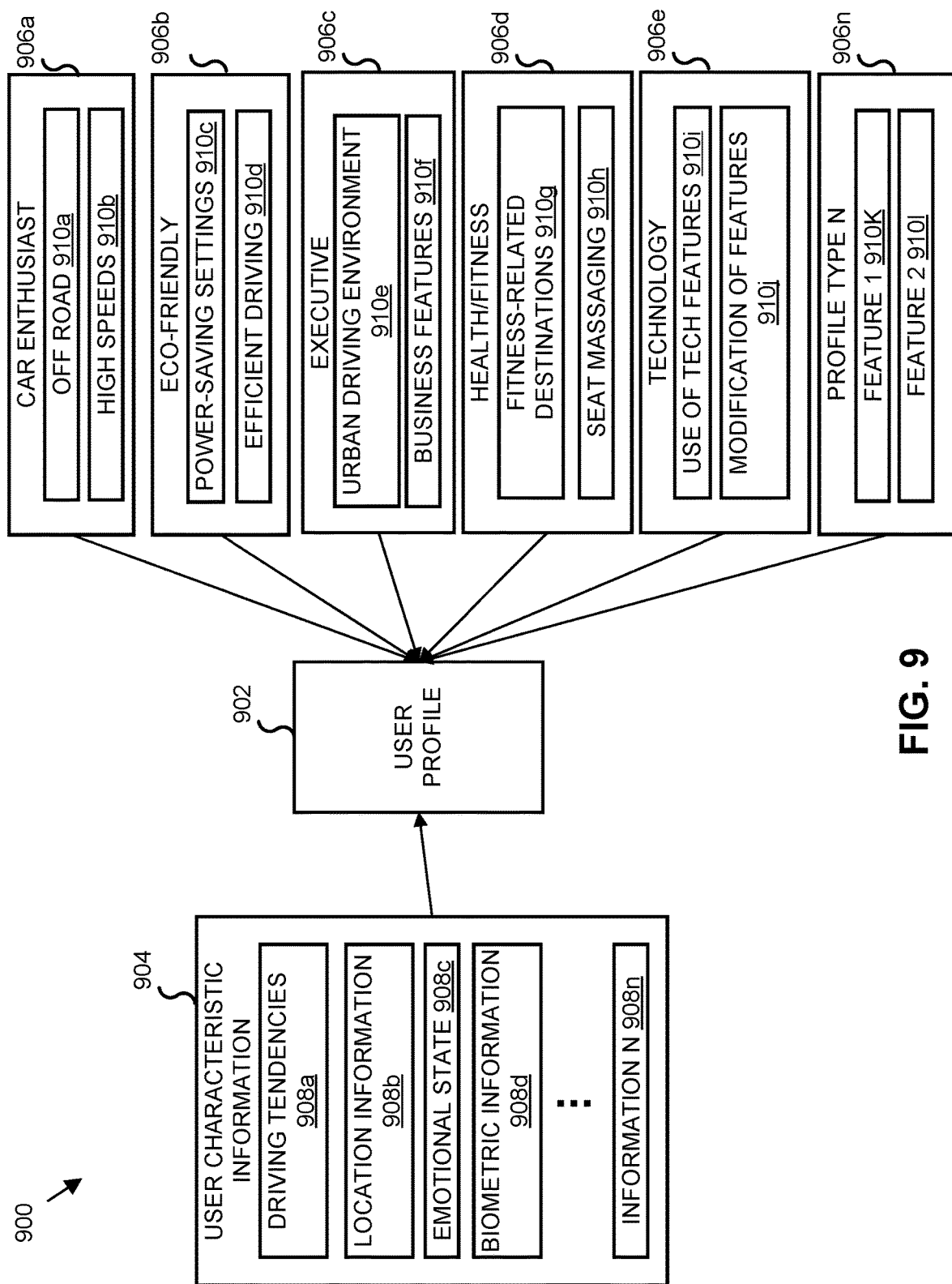
FIG. 9 is an example block diagram for generating a user profile.

FIG. 9 is an example block diagram 900 for generating a user profile. As shown in FIG. 9, a user profile 902 can be based on both user characteristic information 904 and profile types 906a-n. For instance, user characteristic information 902 can be compared with the profile types 906a-n to match a specific feature included in the user characteristic information 902 with a corresponding profile types 906a-n. Example user characteristic information 904 features can include driving tendencies 908a, location information 908b, emotional state 908c, biometric information 908d, and any other information 908n.

As shown in FIG. 9, a feature 908a-n of the user characteristic information 904 can be compared with features 910a-l of each profile type 906a-n to identify a profile type that corresponds to each acquired feature 908a-n. As an example, if a driving tendency 908a indicates that the user operates the vehicle in off-road conditions or in a manual-transmission state, the user profile 902 can identify that a car enthusiast profile 906a corresponds to this driving tendency 908a. Identifying a profile type 906a-n that corresponds to a portion of user characteristic information 904 can include extracting features 908a-n of the portion of user characteristic information 904 and identifying features 910a-l of each profile type 906a-n to identify a profile type that includes a number of similar features that exceeds a threshold level or includes a greatest number of similar features of all profile types.

Upon identifying a profile type 906a-n that corresponds to a portion of user characteristic information 904, the user profile 902 can retrieve features associated with the corresponding profile type and associate those features with user in the user profile 902. As more user characteristic information 904 is acquired, the user profile 902 can be updated with more features that correspond to various profile types 906a-n. In some embodiments, if the user profile 902 includes a number of portions of user characteristic information 904 that corresponds to a profile type that exceeds a threshold similarity, the user profile 902 correlates all features of that profile type to the user profile 902. In other embodiments, the user profile 902 includes features 910a-l of various profile types 906a-n. This may result in the generation of a unique user profile 902 that is specific to each user.

A profile model can be generated that is indicative of user interests that can be used in user-specific info generation. A personalized data processing module may apply a model to the sensor data to determine the state of the vehicle. The model can include any of a variety of classifiers, neural networks, or other machine learning or statistical models enabling the personalized data processing module to determine the vehicle's state based on the sensor data. Once the vehicle state has been determined, the personalized data processing module can apply one or more models to select vehicle outputs to change the state of the vehicle. For example, the models can map the vehicle state to one or more outputs that, when effected, will cause the vehicle state to change in a desired manner.

The machine learning adaptation module can continuously learn about the user of the vehicle as more data is ingested over time. The machine learning adaptation module may receive feedback indicating the user's response to the vehicle experience system outputs and use the feedback to continuously improve the models applied by the personalized data processing module. For example, the machine learning adaptation module may continuously receive determinations of the vehicle state. The machine learning adaptation module can use changes in the determined vehicle state, along with indications of the vehicle experience system outputs, as training data to continuously train the models applied by the personalized data processing module.

User Detection and Identification

In some embodiments, one or more users in a vehicle can be detected using various techniques. Detecting on or more users in the vehicle may allow for retrieval of a user profile of the user that can be used in personalizing output actions in the vehicle.

The set of sensors disposed in the vehicle can be used to detect one or more users in the vehicle. As an example, various biometric information associated with a user can be used in detection of a user. For instance, a camera can capture facial features of a user, and facial recognition techniques can be implemented to identify a user based on the captured facial features of the user. Other examples of biometric information that can be used in user detection can include a weight of the user, a height of the user, a fingerprint of the user, etc.

In some embodiments, detecting a user can include acquiring audio representing a voice of a user and processing the audio to derive a user based on their voice. Processing the voice of the user can include detecting words, phrases, tones, etc. of the voice to identify a user from the voice. The voice of the user can be captured by a microphone disposed in the vehicle.

In some embodiments, detecting a user can include the vehicle connecting to an electronic device associated with the user and identifying the user based on an identifier of the electronic devices that is indicative of the user. For instance, when a mobile phone associated with the user is within a communication range of a communication component (e.g., antenna) of the vehicle, the mobile phone may provide an indicator that identifies the individual.

In some embodiments, a user can be detected responsive to obtaining a password or passcode that is unique to the user. For example, this can include providing a password on an application of a mobile phone associated with the user or providing a password directly to the vehicle.

Upon detecting a user, the vehicle may provide a prompt requesting confirmation of the identity of the user. Upon obtaining a confirmation (e.g., via voice command, a passcode) from the user, the user profile relating to the user can be retrieved.

In some embodiments, multiple users can be individually identified in various regions of a vehicle. For instance, a first user can be detected in a driver seat region of a vehicle and a second user can be detected in a passenger seat region of the vehicle. While various seats of a vehicle are provided as examples herein, the present embodiments may relate to any suitable vehicle or environment that includes multiple users.

Figure 10:
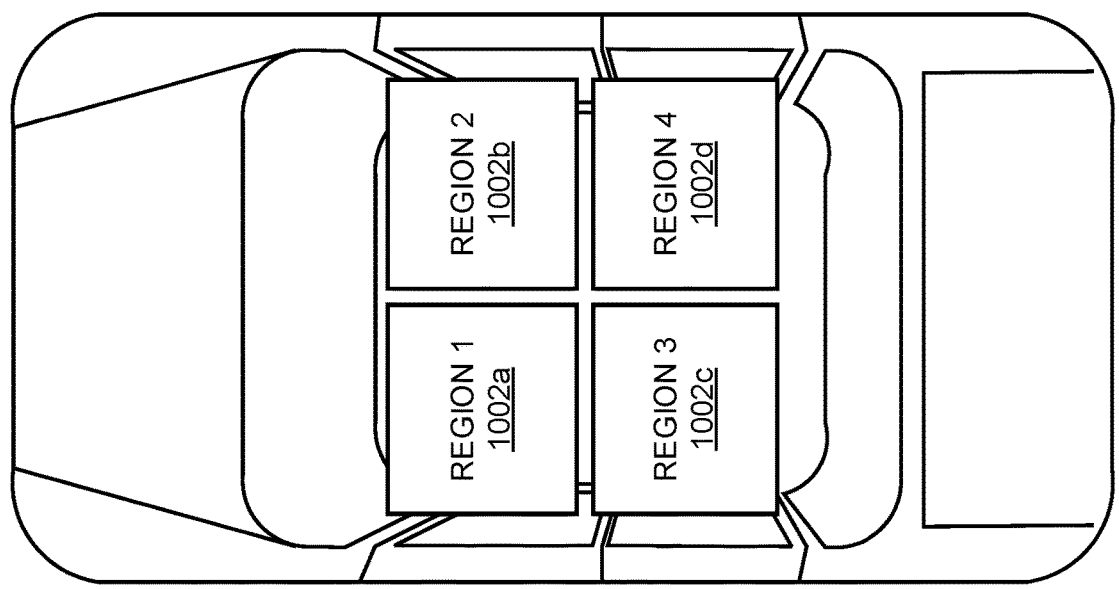
FIG. 10 is a block diagram of an example vehicle with multiple regions.

FIG. 10 is a block diagram of an example vehicle 1000 with multiple regions. As shown in FIG. 10, a vehicle can include multiple regions (e.g., four regions). For instance, a first region 1002a can include a driver seat region, and regions 1002b-d can include passenger seat regions. The series of sensors disposed on the vehicle can identify users located within each region of the vehicle. A unique user can be identified in each region of the vehicle, and a unique user profile for each user can be retrieved and utilized in generating user-specific output actions that are unique to each region.

In some embodiments, the number of features and output actions available to a user in the vehicle can be modified based on a region that the user is located. For instance, while in a first region 1002a, a user may be unable to view video content while the vehicle is operating, while a user in a second region 1002b can view video content without any restriction. As another example, a user in region 4 1002d can modify a brightness level of lights directed toward region 4 1002d, while a user in region 3 1002c can uniquely modify a temperature of the area included in region 3 1002c.

In some embodiments, user profile information can be translated between various vehicles upon identifying the individual. For instance, upon a user entering a rental vehicle, the user profile of the user can be obtained by the rental vehicle. As another example, the user profile can be integrated into a ride-sharing vehicle.

Emotional State Detection

As noted above, an emotional state of a user in the vehicle can be detected. For instance, a series of sensors can inspect facial features and/or biometric information (e.g., a heartbeat) of a user to determine whether the user is stressed or relaxed. Further, detection of an emotional state of a user can be user-specific. In other words, user-specific emotional information can be included in the user profile that can be used in accurately detecting an emotional state of the user based on characteristics that are unique to the user.

Any of the series of sensors disposed in the vehicle can be utilized in detecting an emotional state of the user. For instance, cameras can capture images of the user, and the images can be processed to determine whether facial features of the user indicate that the user is stressed or relaxed.

Further, emotional state information relating to the user can be stored and added to a user profile associated with the user. Particularly, specific features indicative of an emotional state of the user can be added to the user profile that can be utilized in identifying subsequent emotional states of the user. For example, the series of sensors on the vehicle can capture a gaze or a heartbeat of the user. In this example, and of the captured gaze and the heartbeat can be processed to detect an emotional state of the user. For instance, if a heartbeat of the user is greater than an average rate, the detected emotional state may be "stressed." Further, as an example, various heartbeat information (e.g., resting heart-rate, elevated heart rate) can be captured and added to the user profile.

As another example, upon detecting an emotional state of the user, the system may provide a prompt to the user requesting confirmation of the detected emotional state. For instance, the prompt may include the question "We have detected that you are stressed, is that correct?" Upon receipt of a response from the user indicating that the emotional state is correct or incorrect, the particular features that led to the determination of the emotional state can be included as part of the user profile. If the particular features were unique to the user that are indicative of the emotional state, the features can be added to the user profile as being indicative of a particular emotional state.

In some embodiments, the emotional state of a user can be derived from a default set of emotional state characteristics that identify features of each emotional state. As more emotional state information is derived with respect to a user, the default set of emotional state characteristics can be modified for the user and stored as part of the user profile.

Generation of Output Actions

As noted above, any of a number of output actions can be performed based on the user profile and a detected emotional state of the user. An output action can include modification of any suitable feature in a vehicle. Output actions can relate to components interior of the vehicle or exterior of the vehicle. Example components that can be modified by an output action can include interior lighting, audio, video, display settings, seat settings (e.g., heated seats, seat massaging), seat positioning, etc. A central display (or "infotainment system") can also be modified in the output action. For instance, a destination on a mapping application on the infotainment system can be updated.

Figure 11:
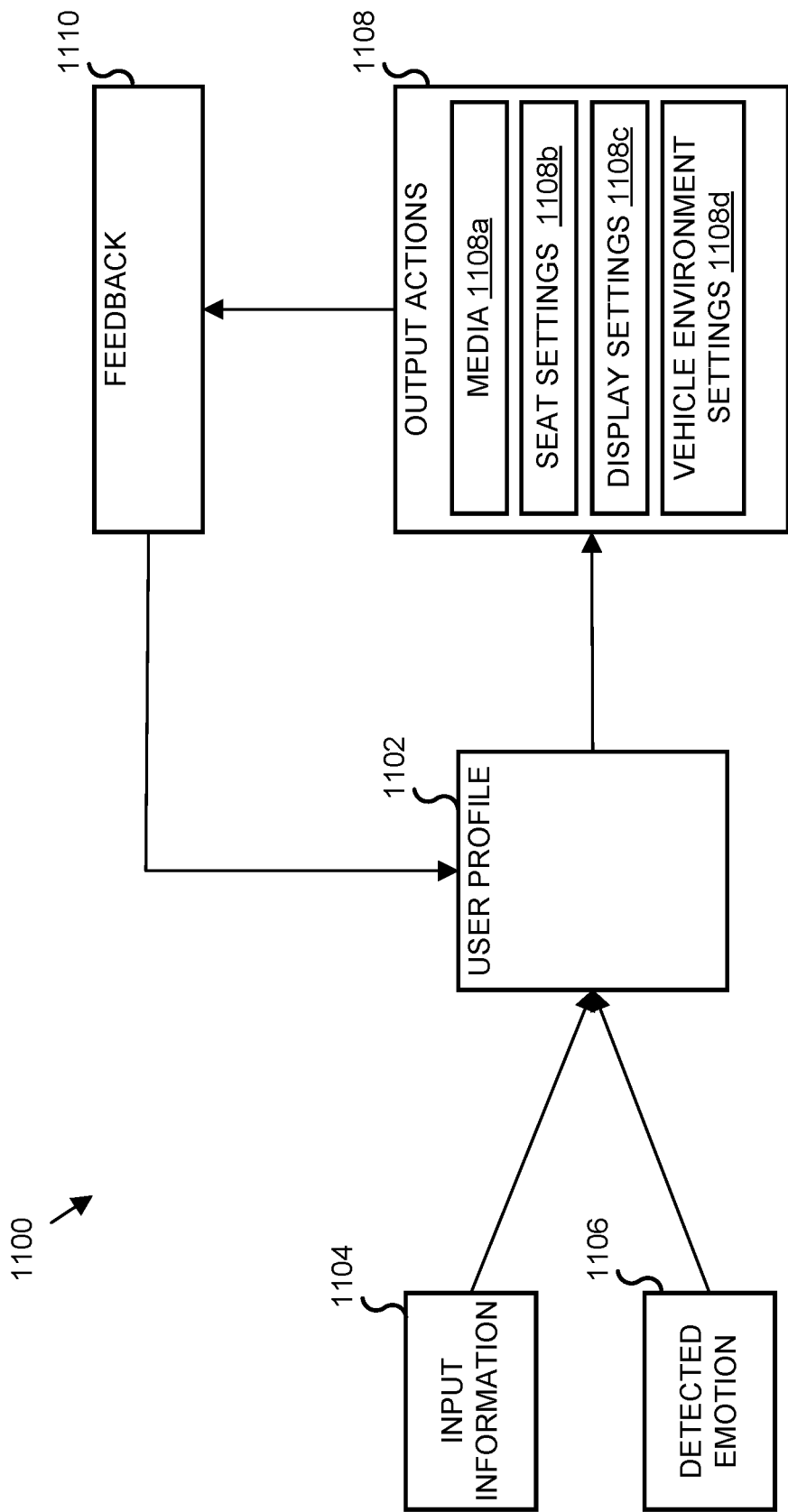
FIG. 11 is an example block diagram for generating personalized output actions.

FIG. 11 is an example block diagram 1100 for generating personalized output actions. As shown in FIG. 11, input information 1104 and a detected emotion 1106 can be obtained. The obtained information can be processed using the user profile 1102 to determine a user-specific output action 1108. Example output actions can relate to media settings 1108a, seat settings 1108b, display settings 1108c, vehicle environment settings 1108d, etc.

As an example, input information 1104 can include destination on an infotainment system and a set of default vehicle interior settings. An example detected emotion 1106 can include an emotion of the user and can be utilized in modifying the output actions.

The user profile 1102 can include user-specific features and a profile type. The profile type can include any profile as described herein. The input information and detected emotion data processed by the user profile can be used to generate output actions.

In some embodiments, feedback information 1110 can be requested from the user. For example, after adjusting the seat settings, feedback 1110 can be provided by the user indicating whether the user confirms the output action. The feedback information can be fed back into the user profile that can be used in subsequent generation of personalized output actions.

In some embodiments, the vehicle environment can interact with other environments. For instance, information can be transmitted between a vehicle and devices included in a smart home environment. Particularly, output actions implemented in the vehicle environment can be translated to another environment.

As an example, upon determining that an output action is to play a song to energize the user, an instruction to play the song on a set of speakers in a smart home environment can be played when the vehicle is within a threshold distance to the smart home environment. In this example, as the user transitions from the vehicle to the smart home environment, the song can transition from the speakers of the vehicle to speakers in the smart home environment. In some embodiments, user characteristic information can be transmitted between devices in various embodiments. For instance, the vehicle can obtain user characteristic information acquired from devices included in a smart home environment.

Output Action Generation Examples

In a first example, a user profile can be associated with an "executive" profile type. The executive profile type can include characteristics that relate to an urban professional. For example, the executive profile type can indicate that the user typically drives on urban roads and highways in congested traffic and that the user has various meetings in their schedule to accommodate.

In this example, upon detecting that an emotional state of the user is relaxed, the system can generate output actions to energize the user. For instance, the output action can include navigating the user to the most-time efficient route to a destination or to present an indication to charge the vehicle between scheduled appointments. Alternatively, detecting that an emotional state of the user is angry or frustrated, the system can generate output actions to relax the user. For instance, the output action can include modifying a destination to stop for a coffee break for the user or to turn on lane assist features on the car to assist with maintaining proper lane positioning of the vehicle to relax the user.

In a second example, a user profile can be associated with a "digital native" profile type. The digital native profile type can include characteristics that relate to a user that utilizes technology features in the vehicle.

In this example, upon detecting that an emotional state of the user is relaxed, the system can generate output actions to energize the user. For instance, the output action can include playing back music with a corresponding dynamic light show in the vehicle or rerouting the destination to a route with lower air quality levels. Alternatively, detecting that an emotional state of the user is angry or frustrated, the system can generate output actions to relax the user. For instance, the output action can include rerouting the destination to stop at a beach or ordering a meal for the user.

In a third example, a user profile can be associated with a "sustainability" profile type. The sustainability profile type can include characteristics that relate to a user that desires to reduce emissions from the vehicle and increases energy efficiency.

In this example, upon detecting that an emotional state of the user is relaxed, the system can generate output actions to energize the user. For instance, the output action can include routing the user to the most energy-efficient route to a destination or presenting a summary of energy efficiency statistics to the user. Alternatively, detecting that an emotional state of the user is angry or frustrated, the system can generate output actions to relax the user. For instance, the output action can include modifying internal climate control responsive to a change in weather or modifying a route to a destination to a scenic route.

In a fourth example, a user profile can be associated with a "health/fitness" profile type. The health/fitness profile type can include characteristics that relate to a user that prioritizes health and wellness-based traits.

In this example, upon detecting that an emotional state of the user is relaxed, the system can generate output actions to energize the user. For instance, the output action can include routing the destination of the vehicle to a gym or directing the user to a parking location farther away from the destination to allow for extra exercise by the user. Alternatively, detecting that an emotional state of the user is angry or frustrated, the system can generate output actions to relax the user. For instance, the output action can include routing the destination to the vehicle to a new restaurant or initiating playback of a sports highlight reel.

In a fifth example, a user profile can be associated with a "car enthusiast" profile type. The car enthusiast profile type can include characteristics that relate to a user that prioritizes performance capabilities of the vehicle.

In this example, upon detecting that an emotional state of the user is relaxed, the system can generate output actions to energize the user. For instance, the output action can include modifying a transmission technique to a sport mode or modifying the destination of the vehicle to a route that optimizes acceleration of the vehicle. Alternatively, detecting that an emotional state of the user is angry or frustrated, the system can generate output actions to relax the user. For instance, the output action can include initiating a driving challenge for the user or reserving a charging station for the user.

Example Method for Identifying and Performing Output Actions in a Vehicle

In some embodiments, the present embodiments relate to performing one or more output actions relating to a modification of at least one feature of a vehicle. For example, an output action can provide modification to various entertainment features (e.g., playback of media), safety features (e.g., lane assist features), and/or comfort features of a vehicle (e.g., interior environment features).

Figure 12:
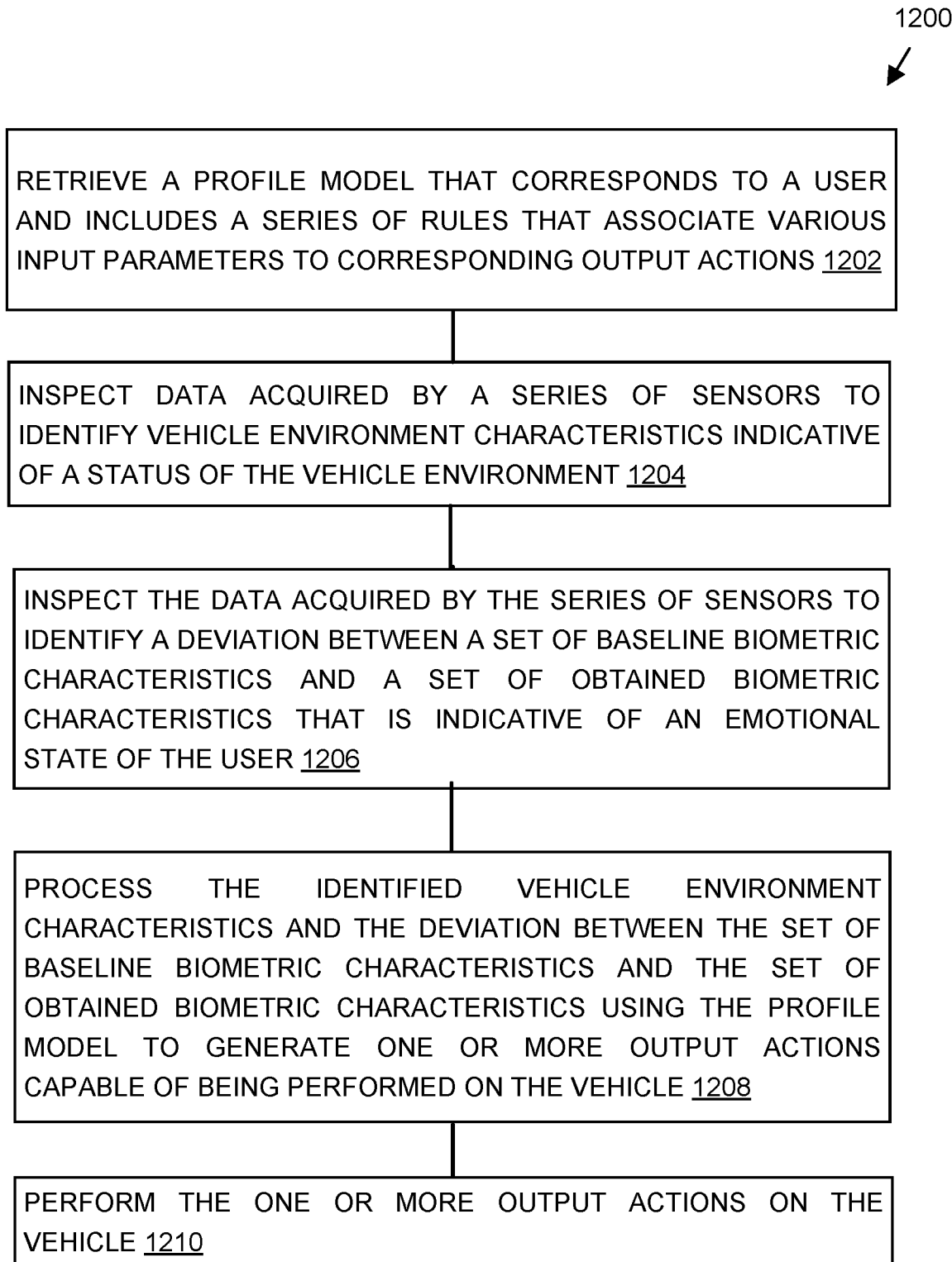
FIG. 12 is a block diagram of an example method for performing one or more output actions relating to a modification of at least one feature of a vehicle.

FIG. 12 is a block diagram of an example method 1200 for performing one or more output actions relating to a modification of at least one feature of a vehicle. The method may include retrieving a profile model that corresponds to a user and includes a series of rules that associate various input parameters to corresponding output actions (block 1202). The profile model can be processed to derive various output actions based on input information. For example, the profile model can be utilized to modify an internal temperature of the vehicle responsive to determining exterior temperature changes. As another example, the profile model can include a rule indicating that at 6 am, the vehicle destination should be routed to the workplace of the user.

The user profile may include a set of user-specific characteristics that correspond to modifications to settings of the vehicle that are specific to the user. The set of user-specific characteristics can modify the series of rules that associate various input parameters to corresponding output actions according to the set of user-specific characteristics. The user profile can include a set of user-specific biometric features that correspond to various emotional states. The various emotional states can include a series of predetermined emotional states with specific features that correspond to each state. For example, detecting that the user is smiling can correspond to a "happy" emotional state.

In some embodiments, the method may include deriving the set of user-specific characteristics in the user profile by comparing the data acquired by the series of sensors with a series of predetermined profile types to identify a predetermined profile type that corresponds to the set of user-specific characteristics. Each predetermined profile type can include characteristics or tendencies common among a subset of individuals. For instance, a predetermined profile type can include a "car enthusiast" profile type that includes features that place an emphasis on utilizing performance features of the vehicle.

In some embodiments, the method may include identifying an identity of the user located within the vehicle. The profile model can be retrieved responsive to identifying the identity of the user. The method can also include detecting other objects in the vehicle, such as cargo or pets, for example, using the techniques as described herein.

In some embodiments, identifying the identity of the user is based on any of comparing biometric data included in the data acquired by the series of sensors with a listing of biometric data of a series of known users and receiving an identification message from a mobile devices associated with the user that is indicative of the identity of the user.

In some embodiments, the method may include identifying a region in the vehicle in which the identified user is located. The one or more output actions can be performed within the identified region. For instance, upon identifying a user in a passenger seat region, climate control features in the passenger seat region can be modified corresponding to the profile model.

The method may include inspecting data acquired by a series of sensors to identify vehicle environment characteristics indicative of a status of the vehicle environment (block 1204). The series of sensors can include any suitable number of sensors disposed exterior or interior of the vehicle as described herein. The data acquired by the sensors can be processed to identify vehicle environment characteristics (e.g., entertainment playback settings, safety feature operation settings, internal climate control settings).

The method may include inspecting the data acquired by the series of sensors to identify a deviation between a set of baseline biometric characteristics and a set of obtained biometric characteristics that is indicative of an emotional state of the user (block 1206). The set of baseline biometric characteristics can include a set of universal biometric characteristics common among a plurality of individuals. For example, a baseline biometric characteristic can include facial features that indicate that the user has a neutral emotional state. The baseline biometric characteristics can be compared to find a derivation with the obtained biometric characteristics of the user. The obtained biometric characteristics can include detected features of the user, such as facial features of the user, a tone of the user's voice, a heart rate of the user, language used by the user, etc. The deviation between the set of baseline biometric characteristics and the set of obtained biometric characteristics can be indicative of an emotional state of the user.

The method may include processing the identified vehicle environment characteristics and the deviation between the set of baseline biometric characteristics and the set of obtained biometric characteristics using the profile model to generate one or more output actions capable of being performed on the vehicle (block 1208).

In some embodiments, processing the identified vehicle environment characteristics and the deviation between the set of baseline biometric characteristics and the set of obtained biometric characteristics using the profile model further comprises comparing the series of rules included in the profile model with a series of vehicle environment characteristics identified from the data acquired by the series of sensors to generate a first series of recommended output actions, and modifying the first series of recommended output actions to include only the one or more output actions based on features derived from the deviation between the set of baseline biometric characteristics and the set of obtained biometric characteristics.

The method may include performing the one or more output actions on the vehicle (block 1210). Output actions can modify various components in the vehicle. For example, various entertainment features, safety features, and/or comfort features can be modified in the output actions.

In some embodiments, the method may include presenting the one or more output actions capable of being performed on the vehicle to the user and receiving an indication to perform a number of the one or more output actions presented to the user, wherein only the number of output actions indicated by the indication are performed on the vehicle.

In some embodiments, the method may include presenting a request for feedback to the user relating to the one or more output actions performed on the vehicle and receiving a response from the user including an indication of whether the one or more output actions performed on the vehicle was appropriate. The profile model may be updated to include the identified vehicle environment characteristics and the deviation between the set of baseline biometric characteristics and the one or more output actions performed on the vehicle.

In some embodiments, the method may include determining that a routed destination of the vehicle is within a threshold distance of an external device environment associated with the user. The method may also include, responsive to determining that the routed destination of the vehicle is within the threshold distance of the external device environment associated with the user, sending an indication to the external device environment including a request to perform output actions that correspond to the one or more output actions performed on the vehicle.

In some embodiments, the method may include determining an operational state of the vehicle that includes an operating state and an idle state, wherein a first subset of output actions are capable of being performed while in the operating state and a second subset of output actions are capable of being performed while in the idle state. For example, the driver may be unable to access video content or game content while the vehicle is in the operating state. In this example, when the vehicle transitions into the idle state (e.g., when the vehicle is parked, the vehicle is charging), other content, such as video content, may become available for the user.

In some embodiments, the method may include inspecting other user characteristic data to generate recommended actions at various points in time. For example, after one hour of continuous driving, the system can provide a message requesting confirmation to the user to stop the vehicle and take a break. The system may recommend various destinations (e.g., a restaurant, coffee shop, gym) to stop. This may include utilizing predictive analysis to estimate a user emotional state based on previously identified emotional state characteristics of the user. For instance, if the user is typically frustrated after work at 6:00 pm, the system can predictively determine that the user is likely to be frustrated and can enable output actions to attempt to relax the user.

In some embodiments, the microphone disposed in the vehicle can be used to determine a noise level in the vehicle. For example, if the microphone detects audio with a greater volume, the user may be more likely to be upset or angry, as the greater volume noises can frustrate the user. The noise level information can be used in detecting the emotional state of the user.

Presentation of User-Specific Entertainment Content in a Vehicle

As noted above, various entertainment features may be available in a vehicle. For instance, components in a vehicle can be configured to playback entertainment content. The playback of entertainment content can be user-specific. For example, audio content that is identified by the user can be played back on speakers in the vehicle.

Further, the present embodiments may relate to user-specific output of entertainment content by processing a user profile model and various input parameters. For example, an emotional state of the user can be detected. In this example, the emotional state of the user can be processed using the user profile model to generate user-specific modifications to entertainment content in the vehicle.

Figure 13:
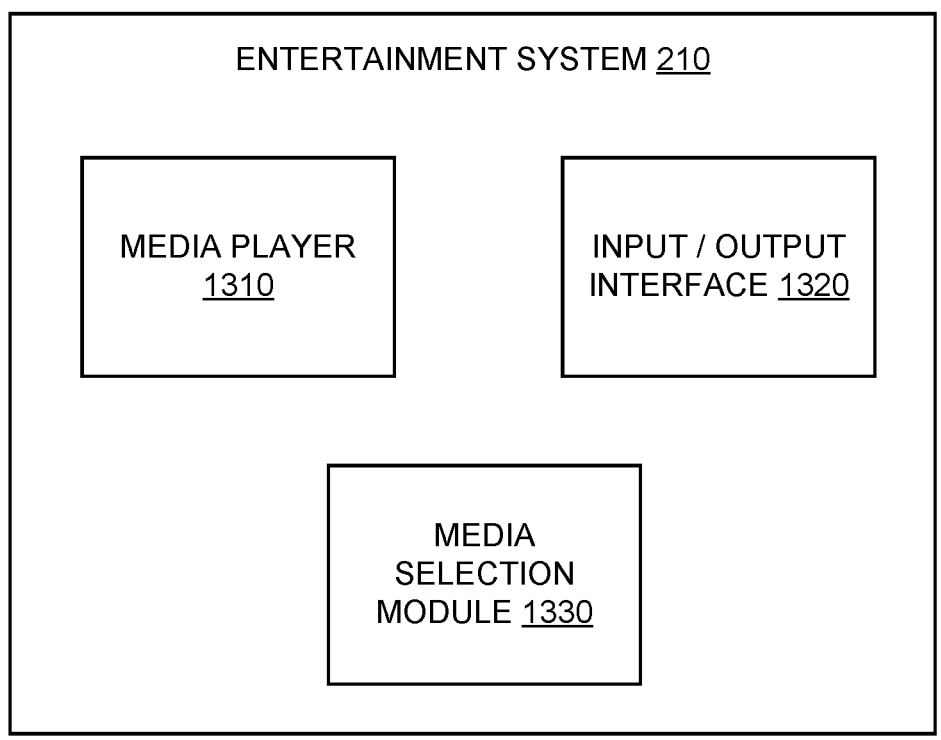
FIG. 13 is a block diagram illustrating functional modules executed by the media system, according to some embodiments.

FIG. 13 is a block diagram illustrating functional modules executed by the entertainment system 210, according to some embodiments. As a part of the entertainment content that can be provided by the entertainment system 210, the entertainment content can select and output media content to a passenger in the vehicle. As shown in FIG. 13, the entertainment system 210 can execute a media player 1310, an input/output interface 1320, and a media selection module 1330. The modules shown in FIG. 13 may comprise software executed by a processor associated with the entertainment system 210, hardware (such as a special-purpose circuit), or a combination of software and hardware. Other embodiments of the entertainment system 210 can include additional, fewer, or different modules, or may distribute functionality differently between the modules.

The media player 1310 retrieves media content and presents the media content for display to the driver via the heads-up display 115. The media player 1310 may be any type of system capable of presenting media content, such as a video player, a music player, a gaming system, a special-purpose application such as a business, productivity, or social media application, or a web browser. The media player 1310 can communicate with the remote servers 150 to retrieve media content for presentation to the driver or passenger in the vehicle 110. In some cases, the media player 1310 may include one or more storage devices, or can be communicatively coupled to a storage device in the vehicle 110 or removably coupled to the vehicle 110, that store media content for presentation to the users. In some embodiments, the entertainment system 210 may include multiple media players 1310, each dedicated to presenting a type of media content (where the presentation can include, for example, depending on the type of the media content, generating interfaces for rendering by the heads-up display 115, outputting audio streams by one or more speakers in the vehicle 110, or receiving inputs to control the media content from the input devices 105).

In some embodiments, where the vehicle 110 is an electric vehicle that periodically needs to be recharged, the media player 1310 provides media in response to detecting that the vehicle 110 has been connected to a charger to recharge the vehicle's battery. For example, the media player 1310 can receive a signal when the vehicle has begun charging, and initiate playback of media content in response to the signal. The media player 1310 can provide the media content throughout the duration of the vehicle charging process.

The input/output (I/O) interface 1320 provides an interface between the entertainment system 210 and input or output devices associated with the vehicle 110. The I/O interface 1320 can receive signals from input devices and process the signals to control respective aspects of the entertainment system 210. Similarly, the I/O interface 1320 can generate output signals and send the signals to output devices to cause an output by the output devices. Output devices in the vehicle 110 can include any of a variety of devices that output signals detectable to the driver, including visual outputs (e.g., the heads-up display 115), audible outputs (e.g., a speaker), tactile outputs (e.g., an input device that provides haptic feedback, a vibration device in the driver's seat that causes the driver's seat to move in association with media content, or a massaging device in the driver's seat that massages the driver), or olfactory outputs (e.g., a device that mists a scent into the air inside the vehicle 110).

The media selection module 1330 selects media to present to the driver. In some cases, the media selection module 1330 selects media in response to a specific request from the driver. For example, the driver selects the media by providing voice input, gesture input, selecting the desired media from a menu, or the like, and the media selection module 1330 retrieves the selected media for the media player 1310 to display to the driver. In other cases, the media selection module 1330 selects media from a preset option. For example, the driver may set a rule to always play a certain game when the vehicle 110 is charging. As another example, the media selection module 1330 may apply a rule to resume content the driver was consuming on another device, such as resuming playback of a video the driver was watching on a home television or resuming review of a document the driver was drafting on a work computer.

In some embodiments, the media selection module 1330 trains a model to select media content for the driver. The model can be trained using data indicating parameters of media content previously provided to the driver and a response of the driver to the provided media content. The model can be generated to output a selection of media content to achieve a desired driver response.

In some embodiments, the model can be trained based on whether the driver changes automatically selected media content to a different type of content, such that the model can be used to determine if a driver is likely to change the media content if specified content is selected. For example, the model may output a determination that the driver always changes a dramatic movie to a comedic movie if the entertainment system 210 selects a dramatic movie to play to the driver. Other features can be used to train the model in addition to an identifier of the selected media content and an indicator of whether the driver changed the selected content, such as a time of day, the driver's schedule, or location of the vehicle. For example, the model may output a determination that the driver usually launches an email application if it is a weekday but usually does not switch away from video content if it is a weekend.

In some embodiments, the model can be trained based on an emotional state of the driver, using the driver's emotional state either as an input to select media content (e.g., given that the driver has a specified emotional state, select certain media content that will appeal to the driver in this state), a desired driver response to the media content (e.g., select media content that will cause the driver to reach a specified emotional state), or both. For example, if the driver is determined to be fatigued, applying the model may cause the media selection module 1320 to select an exercise program as the media content to present to the driver based on a determination that exercise will energize the driver for the remaining of her drive (changing the driver's emotional state from a first state—fatigue—to a second state—energized). As another example, if the driver is determined to be stressed, applying the model may cause the media selection module 1320 to select calming music and switch the driver's seat to a massage mode. The driver's emotional state can be determined as described above.

In some embodiments, the media selection module 1330 determines a modality for presenting media content to the driver, in addition to selecting the content to present. The modality can be determined based on factors such as the type of content, whether the vehicle is moving, location of the vehicle, or the emotional state of the driver. For example, if the media content is a movie that the driver will watch while the vehicle 110 is charging, the media selection module 1330 may select to display the movie across an entirety of (or a substantial portion of) the vehicle's windshield to immerse the driver in the movie. If the driver is instead presented media content that either requires or benefits from contextual awareness, such as an augmented reality game that relies upon the player being able to see an area outside the vehicle, the media selection module 1330 may display the media content within a smaller area that does not block the driver's view of the outside area.

Figure 14:
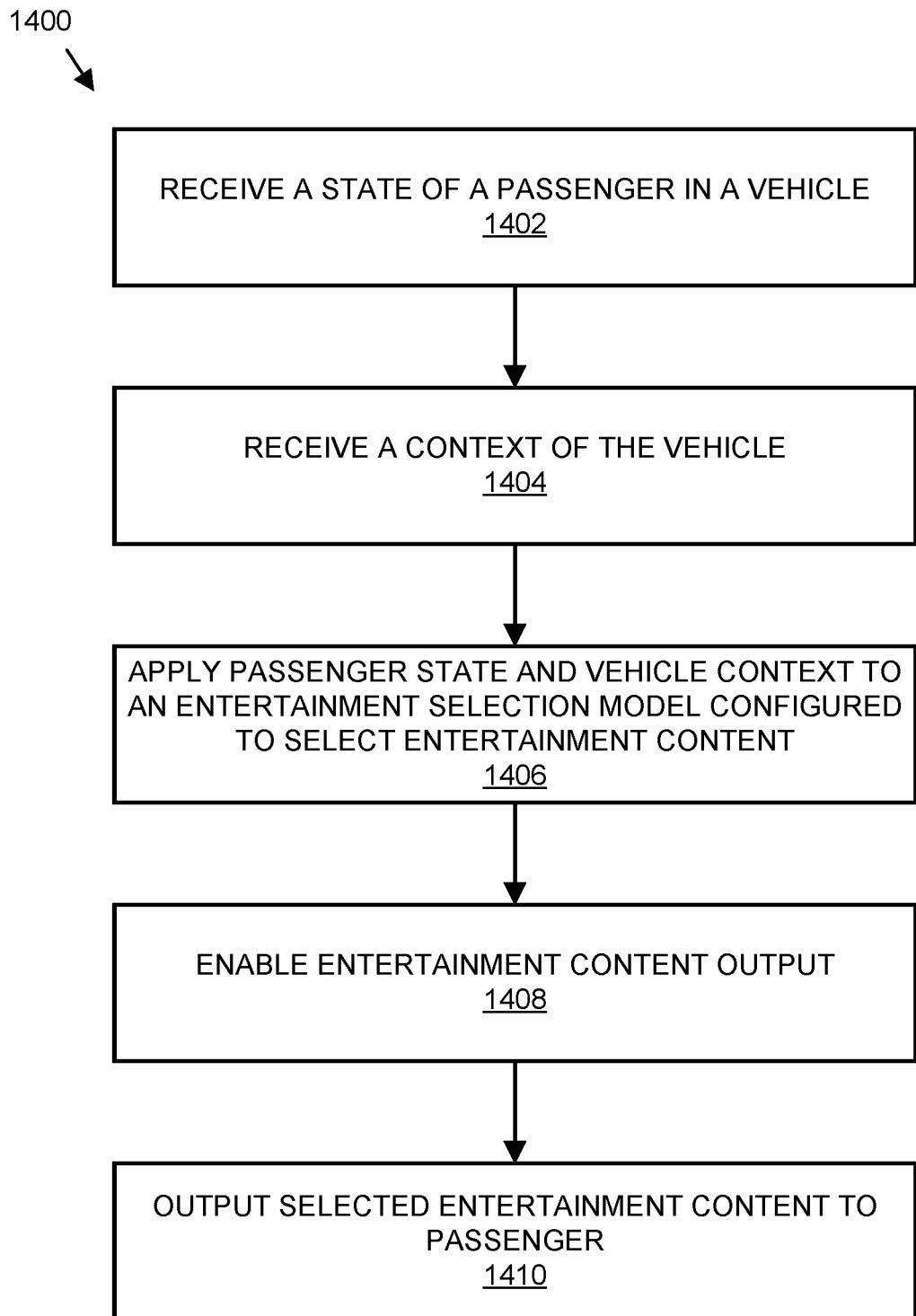
FIG. 14 is a flowchart illustrating an example process for selecting entertainment content for output to a passenger in a vehicle.

FIG. 14 is a flowchart illustrating an example process 1400 for selecting entertainment content for output to a passenger in a vehicle. In the context of FIG. 14, the passenger can include a person who is at least partially involved in driving the vehicle (e.g., a driver) as well as any passive riders in the vehicle. The process 1400 can be performed by the vehicle, for example by the entertainment system 210 in the vehicle. Other embodiments of the process 1400 can include additional, fewer, or different steps, and the steps can be performed in different orders.

As shown in FIG. 14, the vehicle receives, at step 1402, a state of a passenger in the vehicle. The state of the passenger can include at least an emotion of the passenger. The state of the passenger can additionally or alternatively include information about the position of the passenger in the vehicle or an indication of whether the passenger is actively driving the vehicle.

At step 1404, the vehicle receives a context of the vehicle. The context can include, for example, whether the vehicle is moving and, if it is moving, how quickly the vehicle is traveling, a mode of operation of the vehicle (e.g., whether it is operated in a self-driving or manually driven mode), or the like. The context can additionally or alternatively include an indication of a condition in an environment around the vehicle, such as a time of day, a location of the vehicle, a type of road on which the vehicle is traveling (if the vehicle is moving), an amount of traffic on the road, or weather at the vehicle's location.

At step 1406, the vehicle applies an entertainment selection model to at least the passenger state to select entertainment content for the passenger. The entertainment selection model can include a series of input parameters and corresponding output parameters that can be compared with the passenger state to select a selected output parameter that represents selected entertainment content for the passenger.

At step 1406, the vehicle enables output of the entertainment content to the passenger. When the output of the entertainment content is enabled, a passenger can request to receive the entertainment content and the entertainment system 210 will output the entertainment content upon receiving the passenger's request. In contrast, if a passenger requests entertainment content that is not enabled, the entertainment system 210 may deny the request or output a different type of content.

In some embodiments, the vehicle may enable the entertainment content if the context of the vehicle satisfies a condition. For example, entertainment content may be enabled if the vehicle is stopped (e.g., at a charging station) but not enabled if the vehicle is in motion. As another example, entertainment content may be enabled if the vehicle is currently operated in a self-driving mode, or if the vehicle is traveling on a certain type of road. Alternatively, some types of entertainment content can be enabled if the vehicle is stopped or operated in a self-driving mode, while other types of entertainment content are enabled if the vehicle is moving and the passenger is performing at least one of the driving functions of the vehicle. For example, output of music or audiobook recordings may be enabled under any vehicle context, while a video game may only be enabled when the vehicle is parked.

In other embodiments, the vehicle may enable the entertainment content if the passenger's state satisfies a condition. For example, entertainment content may be always enabled for passengers seated in the backseat of a car or for passengers on an airplane. As another example, if the vehicle determines that a driver is more focused on the road when listening to music than when listening to an audiobook, the vehicle may enable music while disabling access to audiobooks if the driver is distracted.

At step 1408, the vehicle outputs the selected entertainment content to the passenger. In some embodiments, the entertainment content is output in response to a request by the passenger. For example, when approaching a charging station, the vehicle may ask the passenger whether he would like to resume playing a selected television show while his vehicle charges. If the passenger confirms, the vehicle can play the selected television show during the charging process. In other embodiments, the entertainment content is output automatically. For example, if a particular type of music is selected for the passenger based on a determination that the passenger is stressed and the music will mitigate the passenger's stress, the vehicle may automatically begin playing the music upon the content's selection.

Example Media System Uses

As a first example use of the entertainment system 210, the system can be used to launch a game while the vehicle 110 is charging. As the vehicle is pulling into a charging station, the entertainment system 210 can prompt the driver to select a game to play (e.g., by asking the driver if she would like to resume the game she played the last time the vehicle was charging). Once the driver selects a game and the vehicle has been connected to the charger, the entertainment system 210 can launch the game and display images associated with the game on the heads-up display 115. In some cases, other components of the vehicle 110 can also be used for inputs or outputs related to the game. For example, the steering wheel of the vehicle may be usable as an input device to control gameplay. The driver's seat may move based on the gameplay, such as transitioning into a rumble seat that moves or vibrates based on the content of or actions taken in the game.

Another example of the entertainment system 210 enables the driver to work while the vehicle 110 is charging. For example, the entertainment system 210 may launch an application related to business or productivity, such as an email application, a word processing application, an integrated development environment, a virtual machine or digital workspace, or the like. The application can be selected, for example, by determining a last item the driver accessed in the vehicle or on another device. For example, if the driver was editing a document in a word processing application running on his work computer before driving to the charging station, the entertainment system 210 can launch a word processing application to resume review of the document while the vehicle is charging. As another example, if the driver received one or more emails while she was driving, the entertainment system 210 may launch an email application to enable the driver to read and respond to the emails.

Yet another example of the entertainment system 210 provides a guided fitness routine that the driver can complete next to the vehicle while the vehicle is charging. For example, if the entertainment system 210 determines that the driver is fatigued and needs to be energized before continuing to drive, the entertainment system 210 may select a fitness routine that instructs the driver to complete one or more exercises. Providing the fitness routine can include displaying a video showing how to perform each exercise in the routine, playing audio describing the exercises, and/or displaying text with instructions for the exercises.

Still another example use of the entertainment system 210 provides social media functionality to facilitate interactions between drivers and passengers at a charging station. For example, a driver can be associated with a profile on a social network. If the driver opts in to the social networking functionality when the driver is stopping at a charging station, the driver's profile can be displayed to other drivers at the charging station via the entertainment system 210 in their vehicles. The driver can also view profiles of the other drivers, as well as optionally the profiles of passengers in the vehicles. The drivers at a charging station at a given time can therefore learn about each other and interact with one another based on the profiles. Presenting the profiles may include, for example, notifying two drivers at a charging station at the same time that they share a common interest, based on the profiles associated with the two drivers including the interest. The drivers can then choose to interact with one another based on the common interest. Presenting the profiles may alternatively include connecting two drivers to compete against each other in a game while they wait for their vehicles to charge. In still another example, the social media functionality can include a dating service. Drivers or passengers who sign up for the dating service can view dating profiles of other drivers or passengers who have signed for the service and who are currently charging their vehicles at the charging station. In some cases, when providing the social media functionality, the entertainment system 210 can facilitate electronic communication between users of the social media services, such as connecting the users to chat electronically while the users remain in their vehicles. In other cases, the entertainment system 210 can facilitate face-to-face communication. For example, the entertainment system 210 can provide information that helps a driver or passenger find another user of the system, such as displaying a picture or description of the user, displaying a picture or description of the vehicle driven by the user, or causing one or both vehicles to output a specified light or sound.

In some cases, the entertainment system 210 can select and provide media content while the vehicle 110 is in motion, in addition to the selection of media content while the vehicle is charging. As an example, the entertainment system 210 can select a type of navigational content to display on the heads-up display 115 while the driver is driving the vehicle 110. Navigational content that gamifies navigation, such as achieving a shortest distance to a destination, achieving a shortest time to the destination, traveling on different roads than usual, or counting a number of a certain type of vehicle or landmark passed, can be selected based on factors such as the driver's emotional state or schedule. For example, if the driver is fatigued, gamified navigational content can be selected that will engage the driver in the process of driving to ensure that he is awake and alert. As another example, if the driver is on her way to a meeting but has time to spare before the meeting starts, gamified or informational navigational content may be selected that takes the driver away from the most efficient route to the meeting, but entertains the driver until the start of the meeting. The navigational content can, for example, route the driver through a historical area near her destination and provide the driver with information about the history of the area as she drives through it. If the driver is stressed and has limited time to reach a destination, the entertainment system 210 can instead display normal navigational content that will route the driver to the destination without overstimulation.

In other examples of providing media content while the vehicle 110 is in motion, the entertainment system 210 can automatically select a type of music to play based on the driver's mood, the driver's schedule, the driver's location, or other factors. The entertainment system 210 can also control how information is displayed via the heads-up display 115 based on the driver's emotional state, time of day, traffic conditions, location, or other factors. For example, the entertainment system 210 can display more information on the heads-up display 115 when the driver is more alert and traffic is light, whereas less information may be displayed if the driver is unfocused and driving through a pedestrian-heavy portion of a city.

In some cases, providers of entertainment content may specify one or more parameters of the vehicle that can be automatically applied to the vehicle or recommended to a passenger when accessing the entertainment content. For example, if the entertainment content is a video, the video provider may specify parameters for the lighting inside the vehicle, volume of the content at various times, brightness of a display device displaying the video, size of the display area, tactile outputs (such as seat vibrations), or olfactory outputs (such as aromatherapy scents emitted throughout the video or at designated times). The provider of the entertainment content can specify the desired parameters through an API of the vehicle experience system 310.

Implementation of User-Specific Comfort-Related Output Actions in a Vehicle

Many vehicle environments include components that facilitate control of features of an internal environment of the vehicle. For example, an internal climate (e.g., temperature, fan speed) of a vehicle can be controlled by a user.

Further, each user in a vehicle generally has a unique set of desired settings for an internal environment of the vehicle. For example, a first user may have a desired internal climate temperature of a first temperature, while a second user has a different desired internal climate temperature that includes a much cooler temperature. Additionally, each user in a vehicle may have differing desired internal environment settings based on various factors, such as a time of day, outside conditions, an emotional state of the user, etc. While internal environment settings are discussed as example comfort-related output actions, any suitable type of comfort-related output actions can be generated.

Accordingly, the present embodiments may relate to generation and implementation of user-specific comfort-related output actions in a vehicle. A user-specific profile model can be used to process input information to generate output actions that modify an internal environment of the vehicle that correspond to desired settings by the user. For example, the user-specific profile model may process a detected emotional state of the user and various vehicle environmental characteristics to generate one or more output actions.

Figure 15:
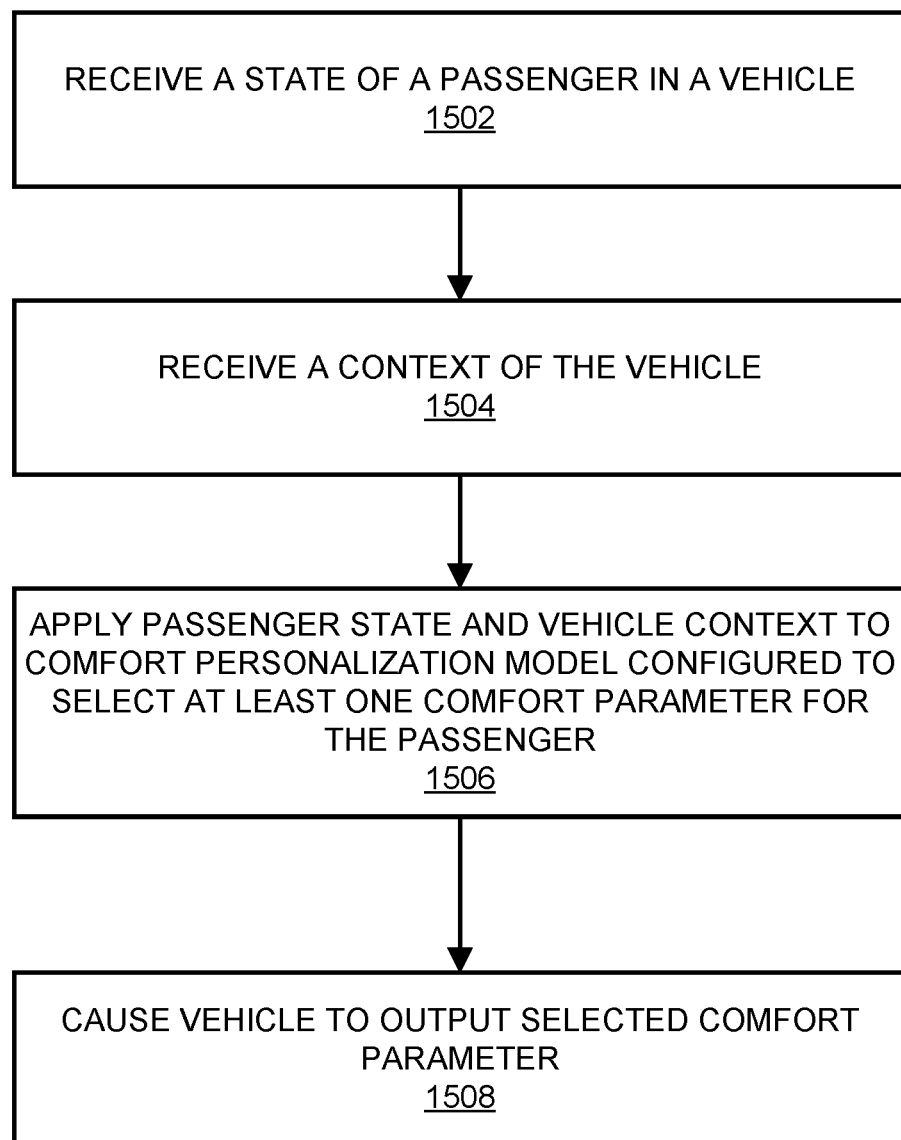
FIG. 15 is a block diagram of an example method for generating and implementing user-specific comfort-related output actions in a vehicle.

FIG. 15 is a block diagram of an example method 1500 for generating and implementing user-specific comfort-related output actions in a vehicle. The method may include receiving a state of a passenger in a vehicle (block 1502). A state of a passenger can include an emotional state of the passenger, for example.

The method may include receiving a context of the vehicle (block 1504). The context of the vehicle can include modifications to various settings of the vehicle. For example, the context of the vehicle can include a modification to a fan intensity setting.

The method may include applying the passenger state and vehicle context information to a comfort personalization model configured to select at least one comfort parameter for the passenger (block 1506). The at least one comfort parameter can include an output action that modifies a comfort-related component in the vehicle, such as a fan or air conditioner, for example.

The method may include causing the vehicle to output the selected comfort parameter (block 1508). This may include modifying a setting of the vehicle relating to the comfort of the user. For example, causing the vehicle to output the selected comfort parameter can include modifying the internal temperature of the vehicle.

Example Method for Performing One or More Output Actions Relating to a Modification to at Least One Internal Environmental Feature of a Vehicle In some embodiments, a method for performing one or more output actions relating to a modification to at least one internal environmental feature of a vehicle includes retrieving a user profile model that corresponds to a user.

In some embodiments, the method may include identifying an identity of the user located within the vehicle, wherein the profile model is retrieved responsive to identifying the identity of the user, wherein identifying the identity of the user is based on any of comparing biometric data included in the data acquired by the series of sensors with a listing of biometric data of a series of known users and receiving an identification message from a mobile device associated with the user that is indicative of the identity of the user.

The method may include inspecting data acquired by a series of sensors disposed on the vehicle to identify a series of vehicle environment characteristics indicative of characteristics of an internal environment of the vehicle;

The method may include inspecting the series of sensors disposed on the vehicle to identify an emotional state of the user. In some embodiments, identifying the emotional state corresponding to the user further comprises inspecting the data acquired by the series of sensors to identify a deviation between a set of baseline biometric characteristics and a set of obtained biometric characteristics that is indicative of the emotional state of the user, and comparing the deviation between the set of baseline biometric characteristics and the set of obtained biometric characteristics with a series of predetermined emotional states to identify a predetermined emotional state with features that correspond to the deviation between the set of baseline biometric characteristics and the set of obtained biometric characteristics.

The method may include processing the identified series of vehicle environment characteristics and the identified emotional state using the user profile model to generate the one or more output actions including modifications to at least one internal environmental feature of the vehicle.

In some embodiments, processing the identified series of vehicle environment characteristics and the identified emotional state using the user profile model further comprises identifying a subset of input actions that are within a threshold similarity of the vehicle environment characteristics, and identifying a number of the subset of input actions that correspond to the data acquired by the series of sensors disposed on the vehicle, wherein the one or more output actions include output actions that correspond to each of the number of the subset of input actions.

The method may include performing the one or more output actions on the vehicle. In some embodiments, the one or more output actions include modifying an internal temperature of the vehicle, modifying a fan speed, modifying an operational state of an aromatherapy diffuser, and modification an operational state of a seat massaging device.

In some embodiments, the method may include presenting a request for feedback to the user relating to the one or more output actions performed on the vehicle, and receiving a response from the user including an indication of whether the one or more output actions performed on the vehicle was appropriate, wherein the user profile model is updated to include the vehicle environment characteristics, the emotional state of the user, and the one or more output actions.

In some embodiments, the method may include determining that a routed destination of the vehicle is within a threshold distance of an external device environment associated with the user, and responsive to determining that the routed destination of the vehicle is within the threshold distance of the external device environment associated with the user, sending an indication to the external device environment including a request to perform output actions that correspond to the one or more output actions performed on the vehicle.

In some embodiments, processing the identified vehicle environment characteristics and the deviation between the set of baseline biometric characteristics and the set of obtained biometric characteristics using the profile model comprises identifying a subset of input actions that are within a threshold similarity of the vehicle environment characteristics, and identifying a number of the subset of input actions that correspond to the deviation between the set of baseline biometric characteristics and the set of obtained biometric characteristics, wherein the one or more output actions include output actions that correspond to each of the number of the subset of input actions.

Implementation of User-Specific Safety-Related Output Actions in a Vehicle

Many vehicle environments include components that facilitate control of safety features of the vehicle. For example, safety features can include a lane-assist feature, a distance control feature, modifying a volume of audio in the vehicle, etc.

The modification of the safety features can be user-specific and/or based on the emotional state of the user. For example, upon determining that a user is frustrated or angry, a lane assist feature may be initiated to assist the user in maintaining a lane position of the vehicle.

The present embodiments may relate to generation and implementation of user-specific safety-related output actions in a vehicle. A user-specific profile model can be used to process input information to generate output actions that modify safety features of the vehicle.

Figure 16:
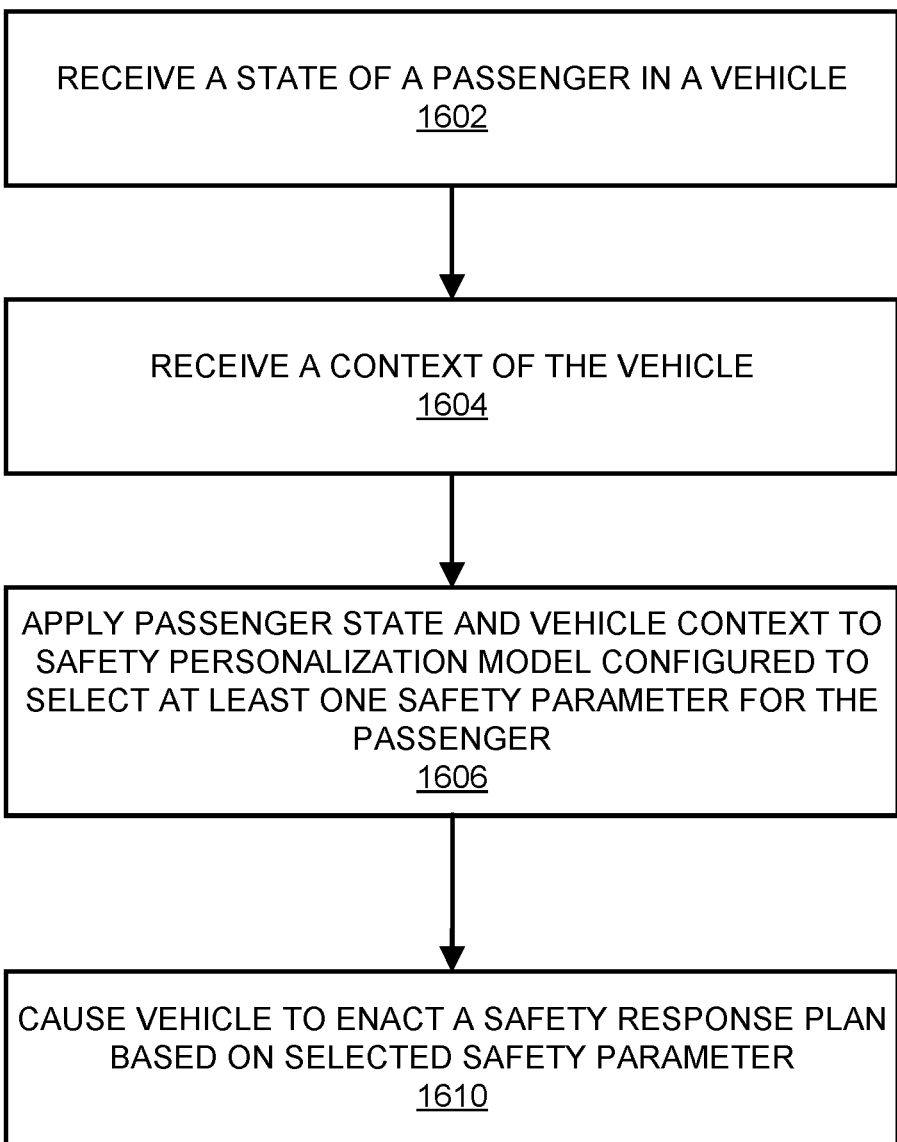
FIG. 16 is a block diagram of an example method for generating and implementing user-specific safety-related output actions in a vehicle.

FIG. 16 is a block diagram of an example method 1600 for generating and implementing user-specific safety-related output actions in a vehicle. The method may include receiving a state of a passenger in a vehicle (block 1602). This may include an emotional state of the user.

The method may include receiving a context of the vehicle (block 1604). The context may include characteristics of the environment interior/exterior to the vehicle and/or user characteristics.

The method may include applying the passenger state and the vehicle context to a safety personalization model configured to select at least one safety parameter for the passenger (block 1606). The at least one safety parameter may include modifying safety features of the vehicle. The method may include causing the vehicle to enact a safety response based on the selected safety parameter (block 1608).

The safety response can be user-specific, as the personalized safety response plan can be based on the emotion detection processes, personalized models, or other systems, processes, or data structures described herein.

Example Method for Performing One or More Output Actions Relating to a Modification to at Least One Vehicle Safety Feature of a Vehicle In some embodiments, a method for performing one or more output actions relating to a modification to at least one safety feature of a vehicle includes retrieving a user profile model that corresponds to a user. The user profile model can include a series of input actions and a series of corresponding output actions that are unique to the user.

In some embodiments, the method can include retrieving user characteristic information that is indicative of user-specific modifications to safety features of the vehicle. The method may also include comparing the retrieved user characteristic information with a series of predetermined profile types to identify a predetermined profile type with features that correspond to the retrieved user characteristic information. The method may also include updating the user profile model with the features associated with the predetermined profile type that corresponds to the retrieved user characteristic information.

The method can include inspecting a set of data acquired by a series of sensors disposed on a vehicle to identify a series of vehicle environment characteristics indicative of a status of safety features of the vehicle and a set of user environmental characteristics relating to features of the user.

The method can include retrieving a series of predetermined emotional states, each predetermined emotional state including a plurality of features indicative of an emotional state.

The method can include comparing the user environmental characteristics with the series of predetermined emotional states to identify a predetermined emotional state with features that correspond to the user environmental characteristics. An emotional state of the user may include the predetermined emotional state.

The method can include processing the identified series of vehicle environment characteristics and the identified emotional state using the user profile model to generate the one or more output actions that are indicative of one or more modifications to any of a series of safety features of the vehicle.

The method can include causing execution of the one or more output actions on the vehicle. In some embodiments, the method can include presenting a request for feedback to the user relating to the one or more output actions performed on the vehicle. In some embodiments, the output actions include any of initiation of a lane position maintenance process, increasing a minimum distance between the vehicle and an adjacent vehicle by a vehicle distance maintenance process, and a reduction of volume of any entertainment content outputting in the vehicle.

The method may also include receiving a response from the user including an indication of whether the one or more output actions performed on the vehicle was appropriate. The user profile model may be updated to include the vehicle environment characteristics, the emotional state of the user, and the one or more output actions.

In some embodiments, the method can include determining an operational state of the vehicle that includes an operating state and an idle state. Only a subset of output actions may be allowed to be performed when in the operating state. The method may also include determining that the operational state of the vehicle has transitioned from the idle state to the operating state. The method may also include, responsive to determining that the operational state of the vehicle has transitioned from the idle state to the operating state, presenting a series of recommended output actions to the user that are capable of being performed in the transitioned operational state. The method may include performing a number of the recommended output actions responsive to obtain a response from the user indicating a confirmation to perform the number of recommended output actions.

In some embodiments, the method can include determining that a routed destination of the vehicle is within a threshold distance of an external device environment associated with the user, and responsive to determining that the routed destination of the vehicle is within the threshold distance of the external device environment associated with the user, send an indication to the external device environment including a request to perform output actions that correspond to the one or more output actions performed on the vehicle.

Example Processing System

Figure 17:
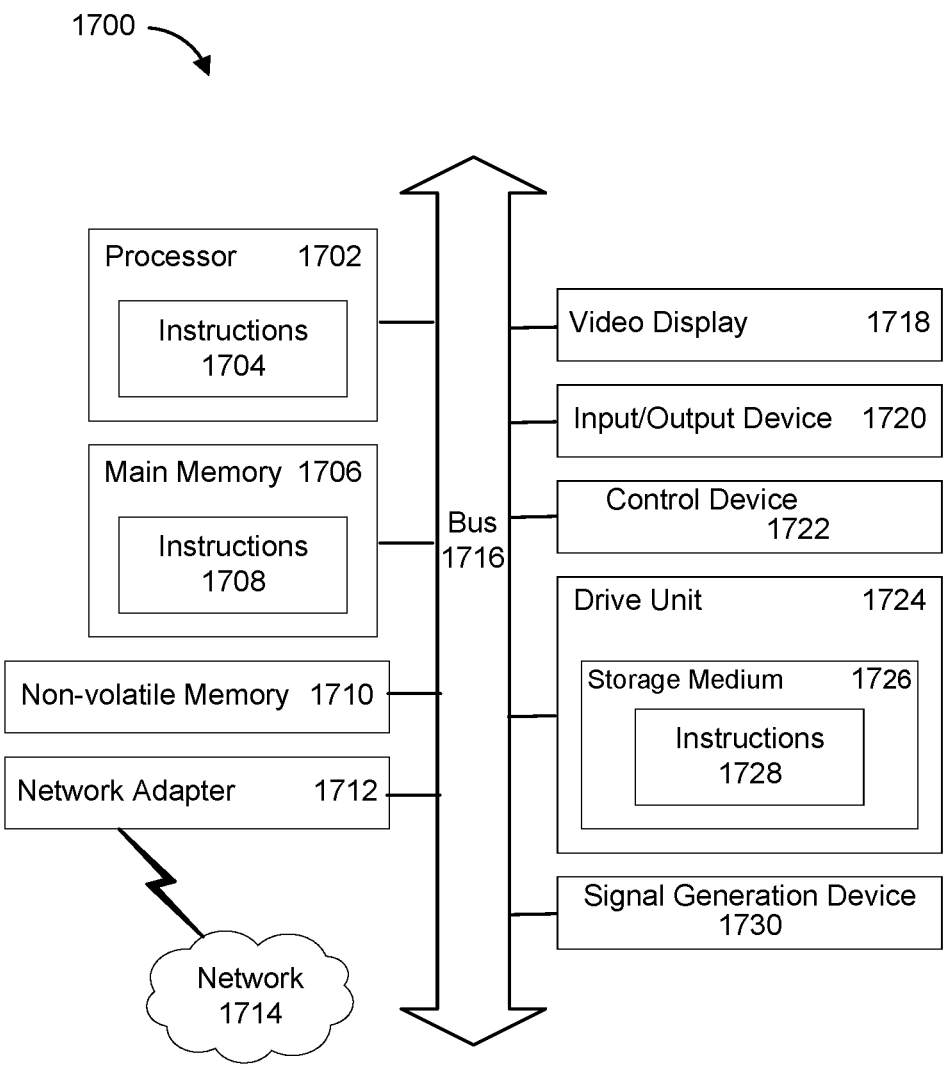
FIG. 17 is a block diagram illustrating an example of a processing system in which at least some operations described herein can be implemented.

FIG. 17 is a block diagram illustrating an example of a processing system 1700 in which at least some operations described herein can be implemented. For example, the remote server 120 may be implemented as the example processing system 1700, and various systems associated with the vehicle 110 may include some or all of the components shown in FIG. 17. The processing system 1700 may include one or more central processing units ("processors") 1702, main memory 1706, non-volatile memory 1710, network adapter 1712 (e.g., network interfaces), video display 1718, input/output devices 1720, control device 1722 (e.g., keyboard and pointing devices), drive unit 1724 including a storage medium 1726, and signal generation device 1730 that are communicatively connected to a bus 1716. The bus 1716 is illustrated as an abstraction that represents any one or more separate physical buses, point to point connections, or both connected by appropriate bridges, adapters, or controllers. The bus 1716, therefore, can include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1794 bus, also called "Firewire."

In various embodiments, the processing system 1700 operates as part of a user device, although the processing system 1700 may also be connected (e.g., wired or wirelessly) to the user device. In a networked deployment, the processing system 1700 may operate in the capacity of a server or a client machine in a client-server network environment, or as a peer machine in a peer-to-peer (or distributed) network environment.

The processing system 1700 may be a server computer, a client computer, a personal computer, a tablet, a laptop computer, a personal digital assistant (PDA), a cellular phone, a processor, a web appliance, a network router, switch or bridge, a console, a hand-held console, a gaming device, a music player, network-connected ("smart") televisions, television-connected devices, or any portable device or machine capable of executing a set of instructions (sequential or otherwise) that specify actions to be taken by the processing system 1700.

While the main memory 1706, non-volatile memory 1710, and storage medium 1726 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 1728. The term "machine-readable medium" and "storage medium" shall also be taken to include any medium that is capable of storing, encoding, or carrying a set of instructions for execution by the computing system and that cause the computing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 1704, 1708, 1728) set at various times in various memory and storage devices in a computer, and that, when read and executed by one or more processing units or processors 1702, cause the processing system 1700 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution. For example, the technology described herein could be implemented using virtual machines or cloud computing services.

Further examples of machine-readable storage media, machine-readable media, or computer-readable (storage) media include, but are not limited to, recordable type media such as volatile and non-volatile memory devices 1710, floppy and other removable disks, hard disk drives, optical disks (e.g., Compact Disk Read-Only Memory (CD ROMS), Digital Versatile Disks (DVDs)), and transmission type media, such as digital and analog communication links.

The network adapter 1712 enables the processing system 1700 to mediate data in a network 1714 with an entity that is external to the processing system 1700 through any known and/or convenient communications protocol supported by the processing system 1700 and the external entity. The network adapter 1712 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1712 can include a firewall which can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

As indicated above, the techniques introduced here implemented by, for example, programmable circuitry (e.g., one or more microprocessors), programmed with software and/or firmware, entirely in special-purpose hardwired (i.e., non-programmable) circuitry, or in a combination or such forms. Special-purpose circuitry can be in the form of, for example, one or more application-specific integrated circuits (ASICs), programmable logic devices (PLDs), field-programmable gate arrays (FPGAs), etc.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A vehicle, comprising:
    a processor; and
    a non-transitory computer readable storage medium storing executable instructions, the instructions when executed by the processor causing the processor to:
        receive a stream of data from a plurality of sensors located in the vehicle that are each configured to measure a different biometric parameter of a person located in an interior of and operating the vehicle;
        during an operating period of the vehicle while a parameter of the interior of the vehicle is in a first state, identify a first emotional state indicator of the person, the first emotional state indicator comprising a first representation generated based on data received from multiple sensors of the plurality of sensors;
        during the operating period of the vehicle, detect a change from the first emotional state to a second emotional state indicator that comprises a second representation generated based on data received from the multiple sensors;
        determine a cause for the change from the first emotional state indicator to the second emotional state indicator; and
        change the parameter of the interior of the vehicle from the first state to a second state based on the determined cause for the change from the first emotional state to the second emotional state.

2. The vehicle of claim 1, wherein the stream of data is received continuously while the vehicle is operated.

3. The vehicle of claim 1, wherein the representations of data comprise at least one of a biometric parameter of the person, voice detection of the person, a facial expression of the person, a body position of the person, or a gesture by the person.

4. The vehicle of claim 1, wherein the first emotional state is a baseline emotional state of the person.

5. The vehicle of claim 1, wherein the instructions when executed further cause the processor to:
    determine a context of an environment external to the vehicle; and
    change the parameter of the interior of the vehicle further based on the context of the environment.

6. The vehicle of claim 1, wherein the parameter of the interior of the vehicle comprises a first setting applied to an entertainment system in the vehicle, and wherein changing the parameter of the vehicle based on the detected change from the first emotional state to the second emotional state comprises changing a setting of the entertainment system from the first setting to a second setting.

7. The vehicle of claim 1, wherein the parameter of the interior of the vehicle comprises a first setting applied to a safety system in the vehicle, and wherein changing the parameter of the vehicle based on the detected change from the first emotional state to the second emotional state comprises changing a setting of the safety system from the first setting to a second setting.

8. The vehicle of claim 1, wherein the parameter of the interior of the vehicle comprises a first setting applied to a comfort system in the vehicle, and wherein changing the parameter of the vehicle based on the detected change from the first emotional state to the second emotional state comprises changing a setting of the comfort system from the first setting to the second setting.

9. A method comprising:
receiving by a processor associated with a vehicle, a stream of data from a plurality of sensors located in the vehicle that are each configured to measure a different biometric parameter of a person located in an interior of the vehicle and operating the vehicle;
during an operating period of the vehicle while a parameter of the vehicle is in a first state, identifying, by the processor associated with the vehicle, a first emotional state indicator of the person, the first emotional state indicator comprising a first representation generated based on data received from multiple sensors of the plurality of sensors;
during the operating period of the vehicle, detecting by the processor associated with the vehicle, a change from the first emotional state indicator to a second emotional state indicator that comprises a second representation generated based on data received from the multiple sensors;
determining by the processor associated with the vehicle, a cause for the change from the first emotional state indicator to the second emotional state indicator; and
changing by the processor associated with the vehicle, the parameter of the vehicle from the first state to a second state based on the determined cause for the change from the first emotional state to the second emotional state.

10. The method of claim 9, wherein the stream of data is received continuously while the vehicle is operated.

11. The method of claim 9, wherein the representations of data comprise at least one of a biometric parameter of the person, voice detection of the person, a facial expression of the person, a body position of the person, or a gesture by the person.

12. The method of claim 9, wherein the first emotional state is a baseline emotional state of the person.

13. The method of claim 9, further comprising:
determining by the processor associated with the vehicle, a context of an environment external to the vehicle; and
changing the parameter of the vehicle further based on the context of the environment.

14. The method of claim 9, wherein the parameter of the vehicle comprises a first setting applied to an entertainment system in the vehicle, and wherein changing the parameter of the vehicle based on the detected change from the first emotional state to the second emotional state comprises changing a setting of the entertainment system from the first setting to a second setting.

15. The method of claim 9, wherein the parameter of the vehicle comprises a first setting applied to a safety system in the vehicle, and wherein changing the parameter of the vehicle based on the detected change from the first emotional state to the second emotional state comprises changing a setting of the safety system from the first setting to a second setting.

16. The method of claim 9, wherein the parameter of the vehicle comprises a first setting applied to a comfort system in the vehicle, and wherein changing the parameter of the vehicle based on the detected change from the first emotional state to the second emotional state comprises changing a setting of the comfort system from the first setting to the second setting.

17. A non-transitory computer readable storage medium storing executable instructions, the instructions when executed by a processor associated with a vehicle causing the processor to:
receive a stream of data from a plurality of sensors located in the vehicle that are each configured to measure a different biometric parameter of a person located in an interior of and operating the vehicle;
during an operating period of the vehicle while a parameter of the vehicle is in a first state, identify a first emotional state indicator of the person, the first emotional state indicator comprising a first representation generated based on data received from multiple sensors of the plurality of sensors;
during the operating period of the vehicle, detect a change from the first emotional state to a second emotional state indicator that comprises a second representation generated based on data received from the multiple sensors;
determine a cause for the change from the first emotional state indicator to the second emotional state indicator; and
change the parameter of the interior of the vehicle from the first state to a second state based on the determined cause for the change from the first emotional state to the second emotional state.

18. The non-transitory computer readable storage medium of claim 17, wherein the representations of data comprise at least one of a biometric parameter of the person, voice detection of the person, a facial expression of the person, a body position of the person, or a gesture by the person.

19. The non-transitory computer readable storage medium of claim 17, wherein the instructions when executed further cause the processor to:
determine a context of an environment external to the vehicle; and
change the parameter of the vehicle further based on the context of the environment.

20. The non-transitory computer readable storage medium of claim 17, wherein the parameter of the vehicle comprises a first setting applied to an entertainment system in the vehicle, and wherein changing the parameter of the vehicle based on the detected change from the first emotional state to the second emotional state comprises changing a setting of the entertainment system from the first setting to a second setting.

21. The non-transitory computer readable storage medium of claim 17, wherein the parameter of the vehicle comprises a first setting applied to a safety system in the vehicle, and wherein changing the parameter of the vehicle based on the detected change from the first emotional state to the second emotional state comprises changing a setting of the safety system from the first setting to a second setting.

22. The non-transitory computer readable storage medium of claim 17, wherein the parameter of the vehicle comprises a first setting applied to a comfort system in the vehicle, and wherein changing the parameter of the vehicle based on the detected change from the first emotional state to the second emotional state comprises changing a setting of the comfort system from the first setting to the second setting.

\* \* \* \* \*